United States Patent [19]

Pollack

[11] Patent Number: 5,809,477
[45] Date of Patent: Sep. 15, 1998

[54] METHOD, APPARATUS AND MEDIUM FOR ALLOCATING BEDS IN A PEDIATRIC INTENSIVE CARE UNIT AND FOR EVALUATING QUALITY OF CARE

[75] Inventor: Murray M. Pollack, Potomac, Md.

[73] Assignee: Children's Research Institute, Washington, D.C.

[21] Appl. No.: 531,695

[22] Filed: Sep. 21, 1995

[51] Int. Cl.[6] .......................... G06F 159/00; G06F 17/60
[52] U.S. Cl. ..................... 705/3; 705/2; 705/5; 705/6; 705/7; 705/8; 705/9
[58] Field of Search ................................... 395/202, 203, 395/205, 206, 207, 208, 209; 705/235, 6, 7, 8, 9

[56] References Cited

U.S. PATENT DOCUMENTS

| 5,501,229 | 3/1996 | Selker et al. ............................. 128/696 |
| 5,594,638 | 1/1997 | Iliff ......................................... 395/202 |
| 5,652,842 | 7/1997 | Siegrist, Jr. et al. .................... 395/203 |

OTHER PUBLICATIONS

Dialog File 621, Acc. # 00298431: "Mediqual (R) Systems Integrates Cognos' Powerray Software", News Release, May 20, 1991, Atlanta, GA. (3 pages).

Dialog File 621, Acc. # 00308857: "Henry Ford Hospital Purchases New APACHE III Man. System", PR Newswire, Sep. 5, 1991, Washington D.C. (2 pages).

Dialog File 434, Acc. # 11886878: "Neonatal Therapeutic Intervention Scoring System . . . ", Gray, et al. *Pediatrics*, 1992, v. 90, n. 4 (Oct.) pp. 561–567 (2 page abstract only), Oct. 1992.

Dialog File 144, Acc. # 12191056: "Does acute physiologic and chronic health evaluation (APACHE II) scoring . . . ?", Shaughnessy, et al. Anathesia and Analgesia, 1995, 81(1), 24–29, (2 page abstract only).

Dialog File 434, Acc. # 13826414: "The Use of APACHE III to Evaluate ICU Length of Stay, Resource Use & Mortality . . . " Becker, et al. Journal of Cardiovascular Surgery, 1995, v. 36, No. 1 (Feb.) pp. 1–11 (2 pages abstract only), Feb. 1995.

Pollack et al., *Pediatric risk of mortality (PRISM) score*, Critical Care Medicine, vol. 16, No. 11. pp. 1110–1116.

Knaus et al., *APACHE II: A severity of disease classification system*, Critical Care Medicine, vol. 13, No. 10, pp. 818–829.

Knaus et al., *Variations in Mortality and Length of Stay in Intensive Care Units*, Annals of Internal Medicine, vol. 118, No. 10, May 15, 1993, pp. 753–761.

Knaus et al., *Clinical Investigations in Critical Care, The APACHE III Prognostic System, Risk Prediction of Hospical Mortality in Critically Ill Hospitalized Adults*, Chest, Dec. 6, 1991, pp. 1619–1636.

*Primary Examiner*—David R. Hudspeth
*Assistant Examiner*—Joseph Thomas
*Attorney, Agent, or Firm*—McDermott, Will & Emery

[57] ABSTRACT

Computer implemented processes are disclosed for quantifying the severity of condition of patients of a pediatric hospital or pediatric intensive care unit. The measure of severity of condition can be used to calculate a probability of death during hospitalization as well as the expected length of stay for a patient, given information gathered about the patient during the initial hours of hospitalization. This information may then be used to determine availability of beds and to provide objective measures of the quality of care provided by a pediatric hospital or part thereof.

27 Claims, 9 Drawing Sheets

METHOD, APPARATUS AND MEDIUM FOR ALLOCATING BEDS IN A PEDIATRIC INTENSIVE CARE UNIT AND FOR EVALUATING QUALITY OF CARE

TECHNICAL FIELD

The invention is directed to the field of Medical Care and more particularly to allocating beds and monitoring the quality of care in a pediatric hospital or pediatric intensive care unit (PICU).

BACKGROUND ART

Intensive care units (ICUs), first introduced in the 1960s, in 1993 accounted for approximately 7% of total U.S. hospital beds, 20% to 30% of hospital costs, and 1% of the U.S. gross domestic product. These economic and institutional consequences have increased the need for outcome evaluation and guidance regarding efficient utilization. Mortality rates, an insensitive measure for an entire hospital, are high enough in ICUs to serve as one reliable performance indicator. Research is underway in identifying clinical risk factors for death and resource utilization for patients in ICUs.

The history of pediatric intensive care has been marked by increasingly sophisticated and concentrated care. Pediatric ICUs (PICUs) are now complex and costly units. With their evolution, new medical and social pressures related to intensive care have simultaneously emerged. Prognostication is a methodology relevant to these pressures that emphasizes the "natural" course of disease rather than other traditional avenues of injury such as mechanisms of disease. When physicians can characterize disease states in a way that accurately define prognosis, new medical and social issues can be addressed.

The Physiologic Stability Index (PSI) is a pediatric severity of illness measure that accurately assesses mortality risk (1–4). The basis for the PSI was the hypothesis that physiologic instability directly reflects mortality risk. The PSI is a subjective score developed previously by a panel of pediatric intensivists. It assesses physiologic instability by sampling 34 variables from seven physiologic systems. The most abnormal value of each variable during the admission day is coded into 75 preassigned variable ranges that reflect the clinical importance of the derangement. Derangements are assigned 1 point if the abnormality is worthy of concern but not necessarily a change in therapy, 3 points if the abnormality is sufficient to cause a change in therapy under most circumstances, and 5 points if the abnormality is life-threatening. Not all variables had 3 or 5-point ranges since abnormality of a single variable might not be sufficient, by itself, to warrant a change in therapy or indicate an immediate life-threatening dysfunction. Three physiologic variables, systolic BP, heart rate, and respiratory rate, were adjusted for age. Mortality predictions calculated from the PSI score included a 4-day average score and an organ system weighted score calculated from the admission of day data.

In 1988, inventor Dr. Murray M. Pollack authored, with others, an article in Volume 16, number 11 of the journal *Critical Care Medicine* entitled "Pediatric Risk of Mortality (PRISM) Score," in which he undertook to reduce the number of physiologic variables required for severity of illness assessment and to obtain an objective weighting of the remaining variables. The result was the Pediatric Risk of Mortality (PRISM) score.

The PRISM scoring methodology, including variables used and the ranges for each variable are set forth hereinafter.

The validity of the PRISM score was tested by predicting outcomes in a validation data set. Its performance was assessed using goodness-of-fit tests in the total validation group, in each ICU separately, in operative and nonoperative patient categories and in diagnostic groups based on the primary system of dysfunction requiring PICU admission. Overall, 105 deaths were observed and 103.9 deaths were predicted. The corresponding mortality rates were 8.6% observed and 8.5% expected. This excellent agreement was confirmed by the Hosmer-Lemeshow goodness-of-fit test for the total validation group ($\chi^2(5)=0.80$, $p>0.95$. In each ICU, the distribution and number of deaths was also well predicted (all $p>0.10$). The observed mortality rates in the individual ICU's ranged from 3.0% to 17.5% ($p<0.001$). Despite this almost six-fold mortality rate difference, the incorporation of a covariate factor for the institutions into the logistic model did not significantly ($p>0.50$) improve the prediction performance, indicating institutional independence of the PRISM score.

When the validation set was categorized into operative and nonoperative status and diagnostic groups, the number and distribution of deaths were also well predicted.

Table 1 compares the use of the PRISM scoring against use of 4 day average PSI and Organ System Weighted PSI techniques.

TABLE 1

Predictor performances

| Predictor | $A_z$ | Specificity at 99% Sensitivity (%) | Sensitivity at 99% Specificity (%) |
|---|---|---|---|
| 4-day average PSI | .89 | 31 | 33 |
| Organ system weighted PSI | .94 | 35 | 59 |
| PRISM[a] | .91 | 30 | 37 |
| 14 variables (range weighting) | .91 | 30 | 37 |
| 14 variables (range weighting, operative classification) | .91 | 38 | 35 |

[a]Comparison of $A_z$'s; PRISM vs. 4-day average PSI; not significant; PRISM vs. organ system weighted PSI, $p < .01$.

The Journal Chest reported on "Risk Prediction of Hospitality Mortality for Critically Ill Hospitalized Adults in Volume 100, No. 6 in December of 1991. It described a system of risk stratification for severely ill hospitalized patients within independently defined patient groups and a predictive equation which used patient data scoring and reference data on major disease categories and treatment location prior to ICU admission to provide risk estimates for hospital mortality for individual ICU patients. This system is based on adult data and adult ICUs. Such information does not permit reasonable inferences about children's mortality risk or about Pediatric Intensive Care Units.

Similarly, the journal *Annals of Internal Medicine* published an article "Variations in Mortality and Length of Stay in Intensive Care Units" in May of 1993 (Vol. 118, No. 10) which also dealt with adult data and specifically excluded "pediatric . . . [intensive] care units."

There is a need for quantitative and unbiased methods of assessing severity of illness. Such methods can have important applications in pediatric intensive care. For example, evaluations of different therapies are difficult to perform without assuring severity of illness equivalency in the experimental and control populations. The testing of new therapies requires identification of patient groups neither too sick nor too healthy to benefit. Cost-containment investigations require both the evaluation of severity of illness as well as therapies. Severity of illness methods that are accurate, unbiased, easy to use, and have wide physician acceptance will further these initiatives.

There is also a need for methods applicable to quality of care assessments. In university or university-affiliated PICUs with intensivists, a common relationship exists between physiologic instability measured early in the ICU course and outcome. This strongly implies that the use of monitoring and therapeutic techniques to detect and treat physiologic instability in a timely and appropriate manner is relatively uniform. Deviations from this practice would result in unexpectedly high mortality rates that could be detected by goodness-of-fit tests. These results were expected since major characteristics of the study units (university hospitals with pediatric intensivists) are generally believed to be associated with high quality of care. There is a need for a scoring system which can be applied to other PICUs to identify factors related to structure or process of intensive care that are associated with quality of care as well as for routine quality assurance studies.

DISCLOSURE OF THE INVENTION

One advantage achieved by the invention is the provision of an objective method of allocating hospital beds to patients awaiting admission based on the severity of illness of the current patient population.

Another advantage achieved by the invention is to simplify and reduce the time and cost required to gather necessary data for quality assurance monitoring in a pediatric hospital or pediatric intensive care unit.

Another advantage achieved by the invention is to simplify the time and cost of data gathering required to determine probabilities of death as a function of the severity of illness of a pediatric hospital or PICU population.

Another advantage of the invention is found in achieving a simple, objective simplification of the prior art PSI evaluation scheme.

Another advantage of the invention is in the creation of a reliable and objective indicator of patient length of stay in a pediatric hospital or intensive care unit adjusted for severity of illness.

Another advantage of the invention lies in providing a method for evaluating the quality of care of a pediatric hospital or part of a pediatric hospital.

Another advantage of the invention lies in the ability to achieve the above-identified advantages using a computer program. Advantageously, the computer program can either be loaded and run on a computer or can be available for distribution on a recording medium, such as on a magnetic diskette.

These advantages are achieved in accordance to the invention by providing a method for allocating beds for a pediatric hospital by obtaining patient information for each patient admitted to the hospital, and determining a score, PRISM III-24, as set forth hereinafter, for the patient; calculating an estimated duration, LOS, for the hospital stay of said each patient based on said score as follows: determining the number of hospital beds in use at a point in time, using the dates of admission and LOS determined for each patient admitted to said hospital, and allocating hospital beds to patients awaiting admission based on said number of hospital beds in use.

The invention is also directed to a method for determining the probable length of stay of a patient in a pediatric intensive care unit by recording patient information for said patient and determining a score, PRISM III-24, as set forth hereinafter for the patient; and calculating an estimated duration, LOS, for the hospital stay of said patient based on said score as follows:

$$LOS = e^{(b_{PRISM\ III\ 24} + d_0 + d_1 x_1 + \ldots + d_p x_p)}$$

where $b_{PRISM\ III\ 24}$=coefficients from PRISM III-24 ranges as follows:

| PRISM III-24 | $b_{PRISM\ III\ 24}$ |
|---|---|
| 0–13 | 0.05823 + 0.530 (PRISM III-24) |
| 14–16 | 1.2725 |
| 17–23 | 3.3365 − 0.1214 (PRISM III-24) |
| 24–27 | 0.5442 |
| 28–34 | 0.3564 |
| >34 | 0 | where $d_0$=0.4167, and where $d_i$ are the coefficients for the following diagnostic groups and $x_i$=1 if the condition is present and $x_i$=0 if the condition is not present, the diagnostic groups and their coefficients being:

| Diagnosis | $d_i$ |
|---|---|
| Oncologic disease | +0.1529 |
| Pneumonia (viral or bacterial) | +0.4291 |
| Central Nervous System infections | +0.3973 |
| Drug overdose | −0.1973 |
| ICU admission for treatment of acute diabetes or its complications | −0.2528 |
| ICU admission for treatment of congenital heart disease (non-operative) | +0.1749 |
| Postoperative | +0.1529 |
| Admission from inpatient area (excluding operating or recovery room | +0.2554 |
| Previous ICU admission during the current hospitalization | +0.1754 |
| Use of mechanical ventilation during the first 24 hours | +0.5102 |

The invention is also directed to a method of objectively rating the severity of a patient's condition by obtaining patient information for a patient; determining a numerical value for each of the following categories of information for the patient by assigning the value indicated by the range in which the patient's information falls or otherwise assigning 0:

| Cardiovascular/Neurologic Vital Signs | | |
|---|---|---|
| 1 Systolic blood pressure (mm Hg) | | |
| Age | Value = 3 | Value = 7 |
| Neonate | 40–55 | <40 |
| Infant | 45–65 | <45 |
| Child | 55–75 | <55 |
| Adolescent | 65–85 | <65 |
| 2. Temperature (degrees Centigrade) | | |
| All ages   <33 or >40.0   Value = 3 | | |
| 3. Mental Status | | |
| All ages   Stupor/Coma   (GCS <8)   Value = 5 | | |
| 4. Heart Rate (beats per minute) | | |
| Age | Value = 3 | Value = 4 |
| Neonate | 215–255 | >225 |
| Infant | 215–225 | >225 |

-continued

| | | |
|---|---|---|
| Child | 185–205 | >205 |
| Adolescent | 145–155 | >155 |
| 5. Pupillary Reflexes | | |
| All Ages | One fixed, one reactive | Value = 7 |
| All Ages | Both fixed | Value = 11 |
| Acid-Base/Blood Gases | | |
| 1. Acidosis (Total $CO_2$ (mmol/L) or pH) | | |
| All Ages | pH 7.0–7.28 or total $CO_2$ 5–16.9 | Value = 2 |
| All Ages | pH <7.0 or total $CO_2$ <5 | Value = 6 |
| 2. pH | | |
| All Ages | 7.48–7.55 | Value = 2 |
| All Ages | >7.55 | Value = 3 |
| 3. $PCO_2$ (mm Hg) | | |
| All Ages | 50.0–75.0 | Value = 1 |
| All Ages | >75.0 | Value = 3 |
| 4. Total $CO_2$ (mmol/L) | | |
| All Ages | >34.0 | Value = 4 |
| 5. $PaO_2$ (mm Hg) | | |
| All Ages | 42.0–49.9 | Value = 3 |
| All Ages | <42.0 | Value = 6 |
| Chemistry Tests | | |
| 1. Glucose | | |
| All Ages | >200 mg/dL or >11.0 mmol/L | Value = 2 |
| 2. Creatinine | | |
| | Value = 2 | |
| Neonate | >0.85 mg/dL or >75 $\mu$mol/L | |
| Infant | >0.90 mg/dL or >80 $\mu$mol/L | |
| Child | >0.90 mg/dL or >80 $\mu$mol/L | |
| Adolescent | >1.30 mg/dL or >115 $\mu$mol/L | |
| 3. Potassium (mmol/L) | | |
| All Ages | >6.9 | Value = 3 |
| 4. Blood Urea Nitrogen (BUN) | | |
| | Value = 3 | |
| Neonate | >11.9 or >4.3 mmol/L | |
| All Other Ages | >14.9 or >5.4 mmol/L | |
| Hematology Tests | | |
| 1. White Blood Cell Count (cells/mm³) | | |
| All ages | <3,000 | Value = 4 |
| 2. Platelet Count (cells/mm³) | | |
| All Ages | 100,000–200,000 | Value = 2 |
| All Ages | 50,000–99,999 | Value = 4 |
| All Ages | <50,000 | Value = 5 |
| 3. Prothrombin Time (PT) or | | |
| Partial Thromboplastin Time (PTT) seconds) | | |
| | Value = 3 | |
| Neonate | PT >22.0 or PTT >85.0 | |
| All Other Ages | PT >22.0 or PTT >57.0 | | and by summing all values to produce an overall score, PRISM III, which is directly indicative of the seriousness of the patient's condition.

There are two types of PRISM III scores, namely PRISM III-12 and PRISM III-24 which differ only in the number of hours (12 or 24) of data collection after admission upon which the scoring is based.

The PRISM III score can then be used to derive a probability of death of the patient during the patient's admission to a pediatric intensive care unit as follows:

P(death)=$1/(1+e^{-R})$, where R is a function of PRISM III information gathered over the first 12 hours of a patient's admission to the hospital. A number of functions can be utilized to calculate R, namely:

R=−5.2560+0.2759(PRISM III-12),

R=−5.5434+0.3441(PRISM III-12)−0.00267(PRISM III-12)$^2$, where (PRISM III-12)$^2$ is the PRISM III-12 term squared, or R=−5.8294+0.3318(PRISM III-12)−0.00265(PRISM III-12)$^2$+0.4899(Pre-ICU care area)−0.6619(operative status)+0.6620(previous ICU admission)−1.7463(acute diagnosis of diabetes)+0.5148(chromosomal anomaly)+0.7634(acute or chronic oncologic disease)+0.6737(acute nonoperative cardiovascular disease)+1.1103(pre-ICU cardiac massage), where pre-ICU care area=1 if the admission is from an inpatient location, excluding the operating room or recovery room; otherwise it=0;

where operative status=1 if postoperative admission; otherwise it=0;

where previous ICU admission=1 if there was a previous ICU admission during current hospitalization; otherwise it=0;

where acute diagnosis of diabetes=1 if acute problem requiring ICU admission is associated with diabetes (such as ketoacidosis); otherwise it=0;

where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where Acute nonoperative cardiovascular disease=1 if the acute problem requiring ICU admission is associated with congenital or acquired cardiac or vascular disease, excluding postoperative care; otherwise it=0; and where Pre-ICU cardiac massage=1 if there has been closed or open chest cardiac massage (cardiac compressions) immediately prior to the PICU admission; otherwise it=0.

The previous method of objectively rating the severity of a patient's condition can be used optionally with PRISM III scoring of patient information for the first 24 hours after admission by calculating a probability of death of the patient during the patient's admission to a pediatric intensive care unit as follows:

P(death)=$1/(1+e^{-R})$, where R is a function of PRISM III information gathered over the first 24 hours of a patient's admission to the hospital.

The corresponding equations to be used with 24 hour data are:

R=−5.5743+0.2652(PRISM III-24),

R=−6.0396+0.3544(PRISM III-24)−0.00304(PRISM III-24)$^2$, where (PRISM III-12)$^2$ is the PRISM III-12 term squared, and R=−6.2833+0.3377(PRISM III-24)−0.00283(PRISM III-24)$^2$+0.4536(Pre-ICU care area)−0.6966(operative status)+0.6650(previous ICU admission)−1.6763(acute diagnosis of diabetes)+0.5568(chromosomal anomaly)+0.7746(acute or chronic oncologic disease)+0.6467(acute nonoperative cardiovascular disease)+1.1197(pre-ICU cardiac massage) where pre-ICU care area=1 if the admission is from an inpatient location, excluding the operating room or recovery room; otherwise it=0;

where operative status=1 if postoperative admission; otherwise it=0;

where previous ICU admission=1 if there was a previous ICU admission during current hospitalization; otherwise it=0;

where acute diagnosis of diabetes=1 if acute problem requiring ICU admission is associated with diabetes (such as ketoacidosis); otherwise it=0;

where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where Acute nonoperative cardiovascular disease=1 if the acute problem requiring ICU admission is associated with congenital or acquired cardiac or vascular disease, excluding postoperative care; otherwise it=0; and where Pre-ICU cardiac massage=1 if there has been closed or open chest cardiac massage (cardiac compressions) immediately prior to the PICU admission; otherwise it=0.

The invention is also directed to a method of objectively rating the severity of a patient's condition using PRISM III-APS scoring by obtaining patient information for a patient; determining a numerical value for each of the categories set forth in hereinafter of information for the patient by assigning the value indicated by the range in which the patient's information falls or otherwise assigning 0; and by summing all values to produce an overall score, PRISM III-APS, which is directly indicative of the seriousness of the patient's condition.

Like the PRISM III scoring systems, the PRISM III-APS scoring system can be used to determine a probability of death of the patient during the patient's admission to a pediatric intensive care unit as follows:

$P(death)=1/(1+e^{-R})$, where R is a function of PRISM III-APS information gathered over the first 12 hours of a patient's admission to the hospital and ln is the natural logarithm.

The corresponding PRISM III-APS equations are:

$R=-5.4935+0.1016(PRISM\ III\text{-}APS)$, $R=-6.0176+0.1410(PRISM\ III\text{-}APS)-0.00051(PRISM\ III\text{-}APS)^2$, where $(PRISM\ III\text{-}APS)^2$ is the PRISM III-APS term squared, $R=-7.0928+0.0706(PRISM\ III\text{-}APS)+0.8080[\ln(PRISM\ III\text{-}APS+1)]$, where ln is the natural logarithm, and $R=-7.3309+0.0700(PRISM\ III\text{-}APS)+0.7301[\ln(PRISM\ III\text{-}APS+1)]+0.5216(\text{previous ICU care area})-0.5399(\text{operative status})+0.5921(\text{previous ICU admission})-1.9775(\text{acute diagnosis of diabetes})+0.5572(\text{chromosomal anomaly})+0.8360(\text{acute or chronic oncologic disease})+0.8266(\text{acute nonoperative cardiovascular disease})+1.0715(\text{pre-ICU cardiac massage})$, where pre-ICU care area=1 if the admission is from an inpatient location, excluding the operating room or recovery room; otherwise it=0;

where operative status=1 if postoperative admission; otherwise it=0;

where previous ICU admission=1 if there was a previous ICU admission during current hospitalization; otherwise it=0;

where acute diagnosis of diabetes=1 if acute problem requiring ICU admission is associated with diabetes (such as ketoacidosis); otherwise it=0;

where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where Acute nonoperative cardiovascular disease=1 if the acute problem requiring ICU admission is associated with congenital or acquired cardiac or vascular disease, excluding postoperative care;

otherwise it=0; and where Pre-ICU cardiac massage=1 if there has been closed or open chest cardiac massage (cardiac compressions) immediately prior to the PICU admission; otherwise it=0.

The invention is also directed to a method of objectively rating the severity of a patient's condition by obtaining patient information for a patient; determining a score PRISM as set forth in hereinafter, determining the seriousness of the patient's condition, by calculating a probability of death of the patient during the patient's admission to a pediatric intensive care unit as follows:

$P(death)=1/(1+e^{-R})$, where R is a function of PRISM information gathered over the first 24 hours of a patient's admission to the hospital and ln is the natural logarithm and $R=-6.6129+0.2864(PRISM)-0.00162(PRISM)^2-0.7482(\text{operative status})+1.1659(\text{chromosomal anomaly})+1.0794(\text{acute or chronic oncologic disease})+0.6620(\text{pre-ICU care area})+1.3707(\text{pre-ICU cardiac massage})$, where $(PRISM)^2$ is the PRISM term squared, where operative status=1 if postoperative admission; otherwise it=0 where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where pre-ICU care area=1 if the admission is from an inpatient location, excluding the operating room or recovery room; otherwise it=0; and where pre-ICU cardiac massage=1 if there has been closed or open chest cardiac massage (cardiac compressions) immediately prior to the PICU admission; otherwise it=0.

The invention is also directed to a method of objectively rating the severity of a patient's condition by obtaining patient information for a patient; determining a score PRISM determining the seriousness of the patient's condition, by calculating a probability of death of the patient during the patient's admission to a pediatric intensive care unit as follows:

$P(death)=1/(1+e^{-R})$, where R is a function of PRISM information gathered over the first 24 hours of a patient's admission to the hospital, where ln is the natural logarithm and where $R=-7.0086+0.2312(PRISM)-0.00103(PRISM)^2-0.9098(\text{operative status})+0.6751(\text{chromosomal anomaly})+0.9064(\text{acute or chronic oncologic disease})+0.9580(\text{pre-ICU care area})+1.3455(\text{pre-ICU cardiac massage})$.

where $(PRISM)^2$ is the PRISM term squared, where operative status=1 if postoperative admission; otherwise it=0 where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where pre-ICU care area=1 if the admission is from an inpatient location, excluding the operating room or recovery room; otherwise it=0; and where pre-ICU cardiac massage=1 if there has been closed or open chest cardiac massage (cardiac compressions) immediately prior to the PICU admission; otherwise it=0.

The invention is also directed to a method for evaluating the quality of care of a pediatric hospital, by, for a group of patients in the hospital during a period of interest, determining the expected lengths of stay, as set forth above, for each patient; for said group of patients, determining the actual lengths of stay, and determining a measure of quality using the expected lengths of stay and the actual lengths of stay or using statistics thereof.

The invention is also directed to a method for evaluating the quality of care of a pediatric hospital, by, for a group of patients in the hospital during a period of interest, determining a probability of death for each patient in said group as set forth above, using the set of probabilities of death for each patient in said group, determining an expected number of deaths for said group; for said group of patients, determining the actual number of deaths, and determining a measure of quality using the expected number of deaths and the actual number of deaths.

The invention is also directed to a computer running a program implementing any of the methods set forth above and to a diskette, memory element or the like containing a computer program implementing any of the methods set forth above.

Still other objects and advantages of the present invention will become readily apparent to those skilled in the art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF DRAWINGS

FIG. 9 is an illustration of one example of a storage medium on which the computer implemented processes of the invention may be encoded for storage, distribution and the like.

BEST MODE FOR CARRYING OUT THE INVENTION

This invention has its genesis in large collection of medical histories gathered from pediatric intensive care units in a large number of locations around the United States. In the process of developing the invention, those medical records were considered, using both judgmental and statistical techniques, from a number of perspectives in an attempt to quantify the factors in a patient's condition which would most likely predict the patient's death. As work continued with the data, the inventor discovered that certain factors were significant in determining a patient's length of stay in a pediatric hospital. Generally, these factors were associated with severity of illness. With further work, the application of these findings to the evaluation of the quality of care of a pediatric hospital became apparent. As work on the invention continued, the methods and techniques developed were captured in a computer program for quick and easy use on a computer. Having the programs available on diskettes facilitated use of the invention on different computers.

Figure 1A:
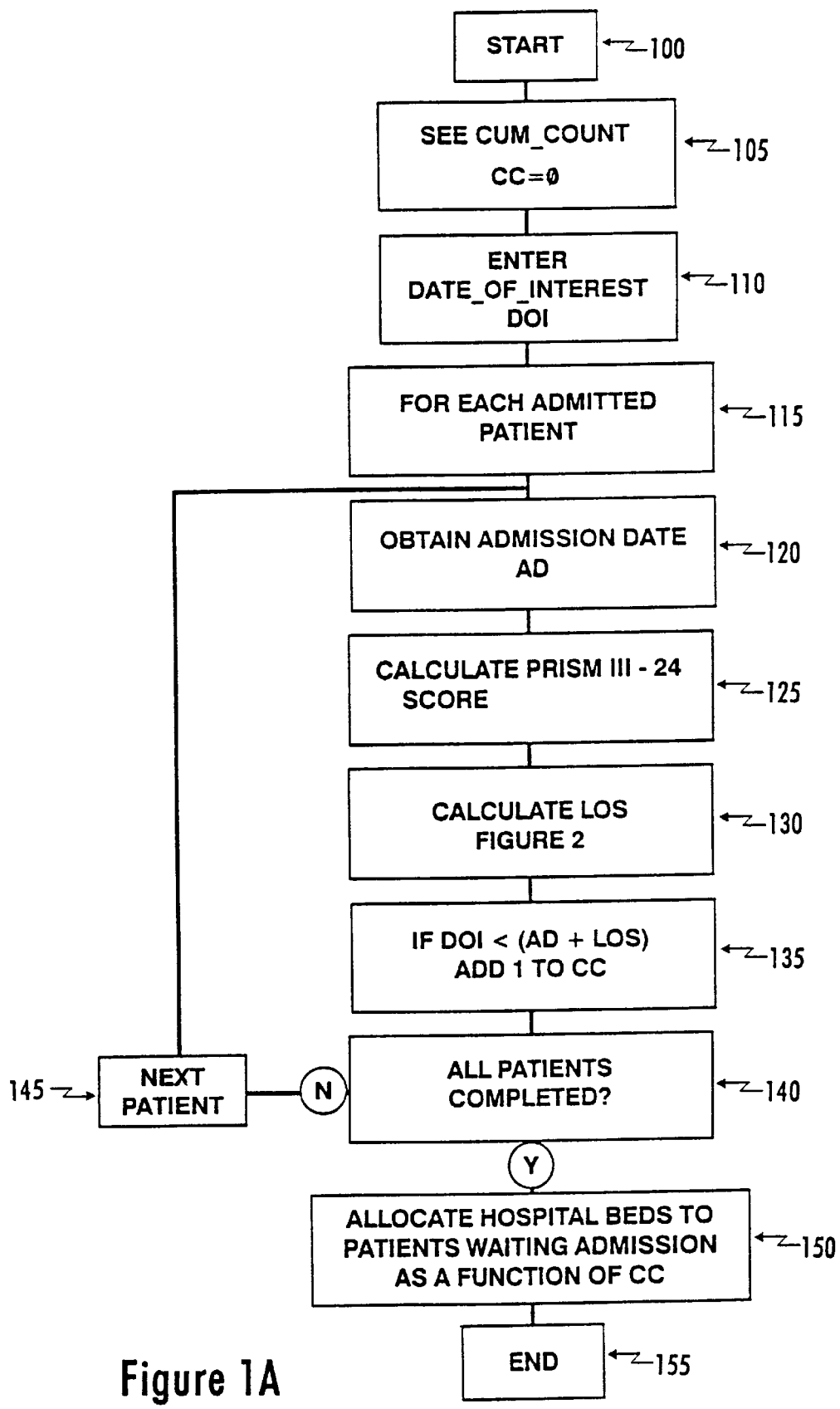
FIG. 1A is a flow chart of a computer implemented process for allocating hospital beds in a pediatric hospital.

FIG. 1a shows a computer implemented process for allocating hospital beds in a pediatric hospital. The process begins at step 100 and a variable CC, representing cumulative count, is set to 0. At item 110, a user enters a date of interest, DOI. The date of interest represents the date with respect to which the user wishes to have the question answered, "How many hospital beds will become vacant between now and the date of interest?" The answer to that question is determined with respect to each patient in the hospital at the time the program is run (115). For each patient, the process obtains, preferably from computerized records, the admission date, AD, of the patient (120). Then, data for that patient is scored using a PRISM III-24 system described hereinafter hereinafter. The -NN suffix to PRISM III indicates the number of hours of data utilized in the scoring. Using that score, an expected length of stay for that patient is determined, utilizing the methodology set forth in FIG. 2 (130). As shown at 135, if the date of interest, DOI, is earlier than the admission date, AD, plus the length of stay, LOS, calculated in 130, a value of 1 is added to cumulative count CC (135). At item 140, a check is made to determine if all admitted patients have been processed and, if not, a next patient is selected at 145 for processing. If all patients have been processed, hospital beds determined to be vacant in a number corresponding to CC are allocated to patients awaiting admission (150). A number somewhat less than CC may be used in lieu of CC to allow for normal variations between expected value and a population's actual value for beds becoming vacant. The process ends at 155.

Figure 1B:
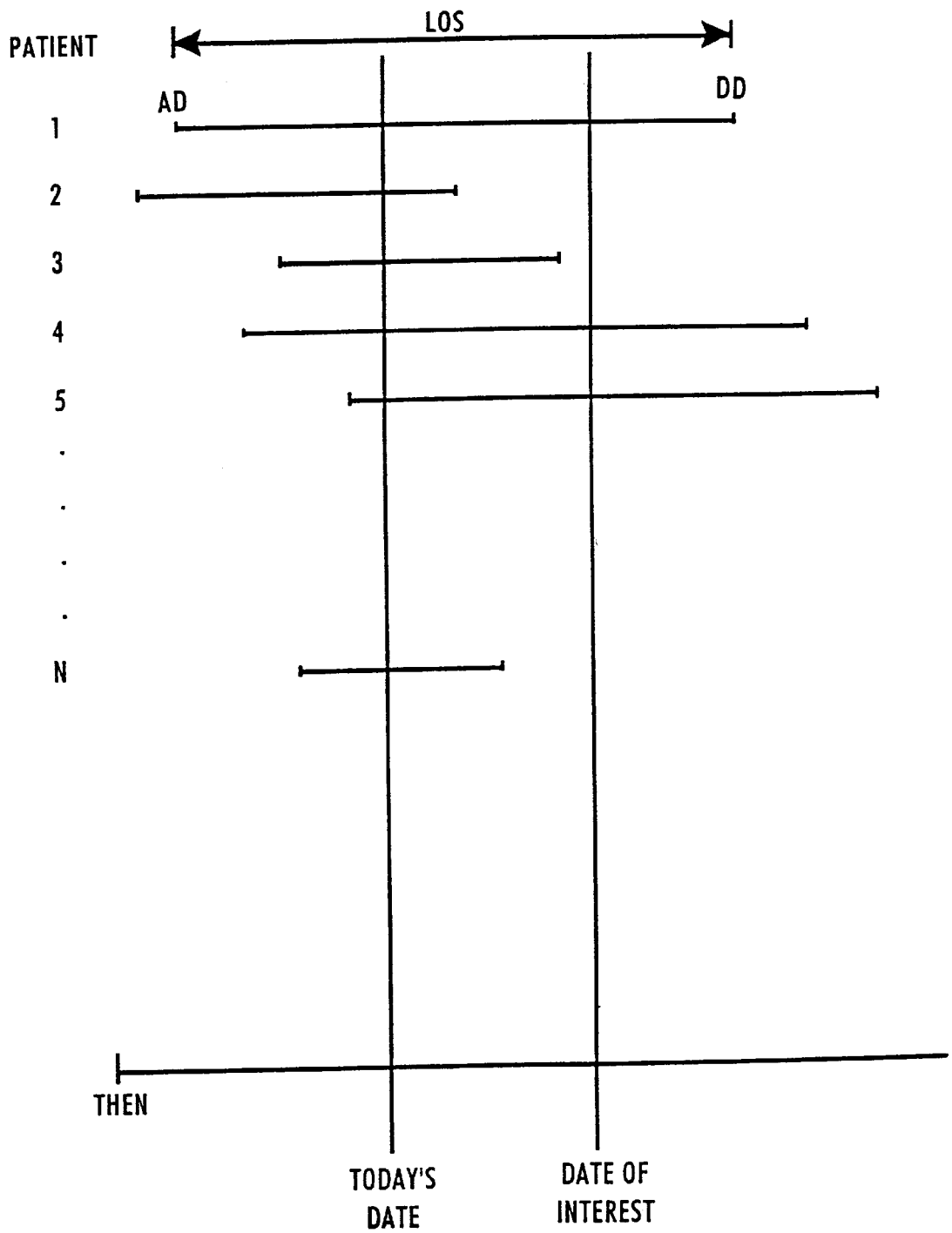
FIG. 1B represents a time line illustrating application of the process of FIG. 1 to a hospital environment.

FIG. 1B is an illustration of the process described in conjunction with FIG. 1a to a patient population consisting of N patients. FIG. 1b represents a time line originating at a time "then" and extending beyond "today's date" to a "date of interest" and beyond. The process described in conjunction with FIG. 1A is illustrated in this manner to facilitate visualization of the process previously described. Each line in FIG. 1B represents a patient and patients are assigned numbers consecutively for convenience of reference. Of the N patients in the hospital on "today's date", only patients 1–5 and N are illustrated. As expected, each of the patients illustrated have a different admission date as indicated by the marks at the left end of the patient's line. The length of the line LOS between admission date, AD, and disposition date, DD, constitutes the length of stay. As can be seen visually, lengths of stay in the hospital are different for different individuals. Typically, a length of stay becomes longer as the severity of the patient's condition increases. However, at some point, if the condition is too severe, the patient dies and the disposition date is thus earlier than might have occurred had the patient been treated to recovery.

Graphically, the question is, given the patient population on today's date, how many beds will be available at some point in the future, namely on the date of interest, given the current patient population. By considering the admission date of each patient and by calculating the length of stay for a patient based on the severity of condition, one may determine an expected number of beds which will become vacant and thus be available for allocation by hospital administration. In the example shown in FIG. 1b, beds from patients 2, 3 and N are expected to become vacant and available for allocation by the date of interest. This is, of course, in addition to any number of beds that may be currently vacant. The number of vacant beds, of course, is a function of the number of beds occupied. Allocation of beds can be done using either of the dual representations, vacant or occupied beds.

Figure 2:
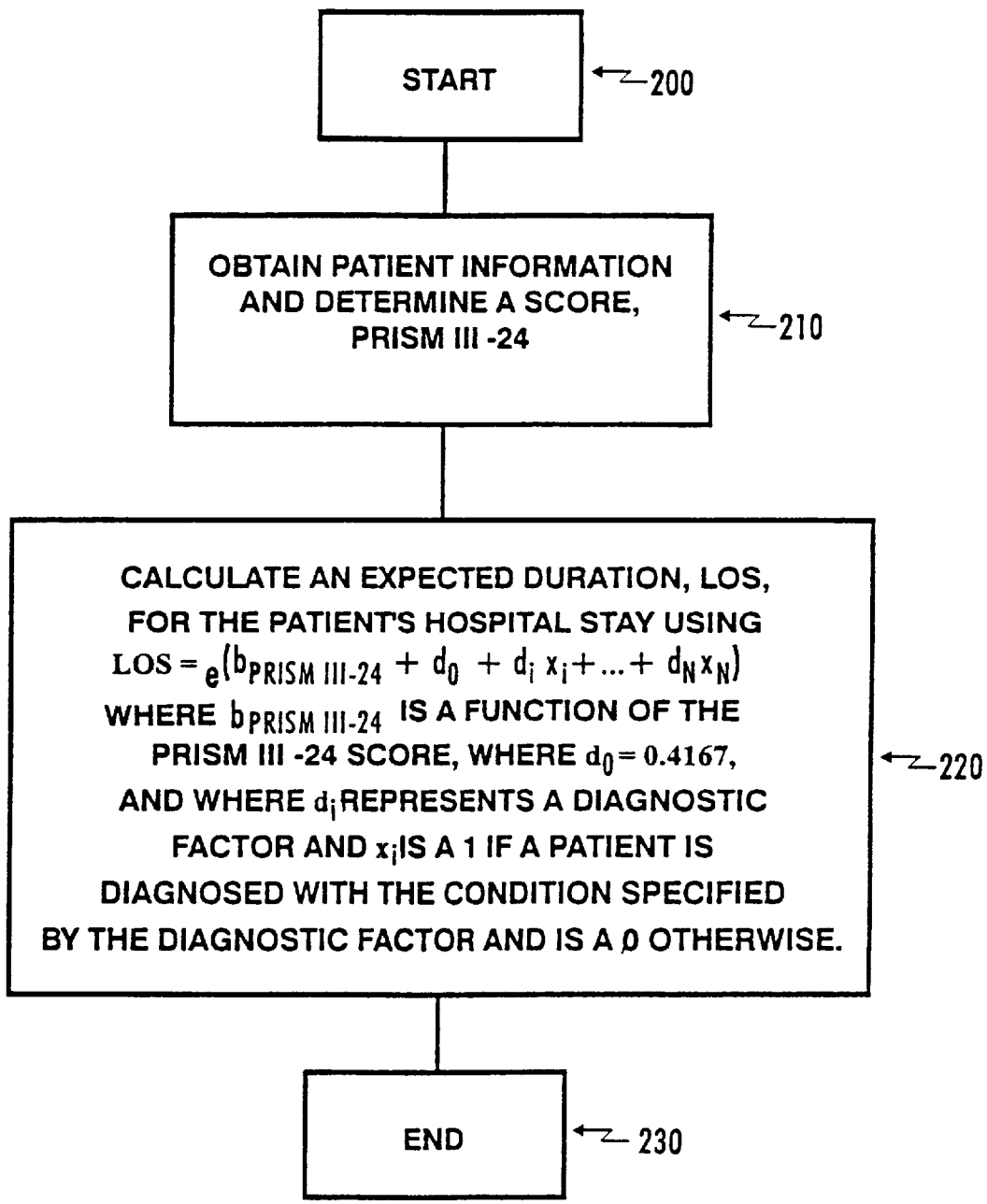
FIG. 2 is a flow chart of a computer implemented process for determining individual length of stay in a pediatric hospital based on severity of the condition of the patient.

FIG. 2 illustrates a computer implemented process for determining an individual's expected length of stay in a pediatric hospital in accordance with the invention. The computer implemented process begins at item 200 and, at 210, patient information for a particular patient is obtained, preferably by retrieval from an automated information system, and a score is determined utilizing the PRISM III-24 methodology described hereinafter.

At step 220, an expected duration, LOS, for the patient's hospital stay is determined using the formula:

$$LOS = e^{(b_{PRISM\ III\ 24} + d_0 + d_1 x_1 + \ldots + d_p x_p)}$$

where $b_{PRISM\ III\ 24}$ = coefficients from PRISM III-24 ranges as follows:

| PRISM III-24 | $b_{PRISM\ III\ 24}$ |
|---|---|
| 0–13 | 0.05823 + 0.530 (PRISM III-24) |
| 14–16 | 1.2725 |
| 17–23 | 3.3365 − 0.1214 (PRISM III-24) |
| 24–27 | 0.5442 |
| 28–34 | 0.3564 |
| >34 | 0 | where $d_0 = 0.4167$, and where $d_i$ are the coefficients for the following diagnostic groups and $x_i = 1$ if the condition is present and $x_i = 0$ if the condition is not present, the diagnostic groups and their coefficients being:

| Diagnosis | $d_i$ |
|---|---|
| Oncologic disease | +0.1529 |
| Pneumonia (viral or bacterial) | +0.4291 |
| Central Nervous System infections | +0.3973 |
| Drug overdose | −0.1973 |
| ICU admission for treatment of acute diabetes or its complications | −0.2528 |
| ICU admission for treatment of congenital heart disease (non-operative) | +0.1749 |
| Postoperative | +0.1529 |
| Admission from inpatient area (excluding operating or recovery room | +0.2554 |
| Previous ICU admission during the current hospitalization | +0.1754 |
| Use of mechanical ventilation during the first 24 hours | +0.5102 |

The diagnostic factors referred to in FIG. 2 are those set forth above. When the length of stay has been calculated, the process ends at block 230.

Three techniques are disclosed herein for scoring a patient, namely, PRISM III-12, PRISM III-24, and PRISM III-APS. Additionally, a fourth technique identified only as PRISM was described by the inventor and others in a prior art publication referenced in the background of the invention. The PRISM methodology is set forth as follows:

PRISM SCORING

| Variable | Age Restrictions and Ranges | | Score |
|---|---|---|---|
| Systolic BP (mm Hg) | Infants | Children | |
| | 130–160 | 150–200 | 2 |
| | 55–65 | 65–75 | |
| | >160 | >200 | 6 |
| | 40–54 | 50–64 | |
| | <40 | <50 | 7 |
| Diastolic BP (mm Hg) | all ages | | 6 |
| | >110 | | |
| HR (beat/min) | Infants | Children | |
| | >160 | >150 | 4 |
| Respiratory rate (breath/min) | Infants | Children | |
| | 61–90 | 51–70 | 1 |
| | >90 | >70 | 5 |
| | Apnea | Apnea | |
| $PaO_2/FIO_2$[a] | all ages | | |
| | 200–300 | | 2 |
| | <200 | | 3 |
| $Paco_2$[b] (torr) | all ages | | |
| | 51–65 | | 1 |
| | >65 | | 5 |
| Glasgow Coma Score[c] | all ages | | |
| | >8 | | 6 |
| Pupillary Reactions | all ages | | |
| | unequal or dilated | | 4 |
| | fixed and dilated | | 10 |
| PT/PTT | all ages | | |
| | 1.5 × control | | 2 |
| Total bilirubin (mg/dl) | >1 mo | | |
| | >3.5 | | 6 |
| Potassium (mEq/L) | all ages | | |
| | 3.0–3.5 | | 1 |
| | 6.5–7.5 | | |
| | <3.0 | | 5 |
| | >7.5 | | |
| Calcium (mg/dl) | all ages | | |
| | 7.0–8.0 | | 2 |
| | 12.0–15.0 | | |
| | <7.0 | | 6 |
| | >15.0 | | |
| Glucose (mg/dl) | all ages | | |
| | 40–60 | | 4 |
| | 250–400 | | |
| | <40 | | 8 |
| | >400 | | |

PRISM SCORING

| Variable | Age Restrictions and Ranges | Score |
|---|---|---|
| Bicarbonate[d] (MEq/L) | all ages <16 >32 | 3 |

[a] Cannot be assessed in patients with intracardiac shunts or chronic respiratory insufficiency; requires arterial blood sampling.
[b] May be assessed with capillary blood gases.
[c] Assessed only if there is known or suspected CNS dysfunction; cannot be assessed in patients during iatrogenic sedation, paralysis, anesthesia, etc. Score <8 correspond to coma or deep stupor.
[d] Use measured values.

The PRISM III-12 and PRISM III-24 are both set forth (differing only in the duration of time (12 hours vs 24 hours) over which data is collected) as follows:

PRISM III SCORING

Cardiovascular/Neurologic Vital Signs
1. Systolic blood pressure (mm Hg)

| Age | Value = 3 | Value = 7 |
|---|---|---|
| Neonate | 40–55 | <40 |
| Infant | 45–65 | <45 |
| Child | 55–75 | <55 |
| Adolescent | 65–85 | <65 |

2. Temperature (degrees Centigrade)
All ages <33 or >40.0 Value=3
3. Mental Status
All ages Stupor/Coma (GCS <8) Value=5
4. Heart Rate (beats per minute)

| Age | Value = 3 | Value = 4 |
|---|---|---|
| Neonate | 215–255 | >225 |
| Infant | 215–225 | >225 |
| Child | 185–205 | >205 |
| Adolescent | 145–155 | >155 |

5. Pupillary Reflexes
All Ages One fixed, one reactive Value=7
All Ages Both fixed Value=11

Acid-Base/Blood Gases

1. Acidosis (Total $CO_2$ (mmol/L) or pH)
All Ages pH 7.0–7.28 or total $CO_2$ 5–16.9 Value=2
All Ages pH <7.0 or total $CO_2$<5, Value=6
2. pH
All Ages 7.48–7.55 Value=2
All Ages >7.55 Value=3
3. $PCO_2$ (mm Hg)
All Ages 50.0–75.0 Value=1
All Ages >75.0 Value=3
4. Total $CO_2$ (mmol/L)
All Ages >34.0 Value=4
5. $PaO_2$ (mm Hg)
All Ages 42.0–49.9 Value=3
All Ages <42.0 Value=6

Chemistry Tests
1. Glucose
All Ages >200 mg/dL or >11.0 mmol/L Value=2

2. Creatinine

| | Value = 2 |
|---|---|
| Neonate | >0.85 mg/dL or >75 μmol/L |
| Infant | >0.90 mg/dL or >80 μmol/L |
| Child | >0.90 mg/dL or >80 μmol/L |
| Adolescent | >1.30 mg/dL or >115 μmol/L |

3. Potassium (mmol/L)
All Ages >6.9 Value=3
4. Blood Urea Nitrogen (BUN)

| | Value = 3 |
|---|---|
| Neonate | >11.9 or >4.3 mmol/L |
| All Other Ages | >14.9 or >5.4 mmol/L |

Hematology Tests
1. White Blood Cell Count (cells/mm³)
All ages <3,000 Value=4
2. Platelet Count (cells/mm³)

| All Ages | 100,000–200,000 | Value = 2 |
|---|---|---|
| All Ages | 50,000–99,999 | Value = 4 |
| All Ages | <50,000 | Value = 5 |

3. Prothrombin Time (PT) or Partial Thromboplastin Time (PTT) seconds)

| | Value = 3 |
|---|---|
| Neonate | PT >22.0 or PTT >85.0 |
| All Other Ages | PT >22.0 or PTT >57.0 |

Notes:
1. PRISM III mortality risk equations are available for the first 12 hours and the first 24 hours of PICU care.
2. General: Use the highest and/or the lowest values for scoring. When there are both low and high ranges, PRISM III points may be assigned for the low and the high ranges. Readmissions are included as separate patients. Exclude admissions routinely cared for in other hospital locations, staying in the PICU <2 hours; and those admitted in continuous CPR who do not achieve stable vital signs for ≧2 hours. Deaths occurring in the OR are included only if the operation occurred during the PICU stay and was a therapy for the illness requiring PICU care. Terminally ill patients transferred from the PICU for "comfort care" are included as PICU patients for the 24 hours following PICU discharge or, if receiving technologic support, until 24 hours after the technologic support is discontinued. Ages: Neonate=0–<1 month; Infant=1 month–<12 months; Child=12 months–<144 months; Adolescent ≧144 months.
3. Heart Rate: Do not assess during crying or iatrogenic agitation.
4. Temperature: Use rectal, oral, blood, or axillary temperatures.
5. Pupillary Reflexes: Nonreactive pupils must be >3 mm. Do not assess after iatrogenic pupillary dilation.
6. Mental Status: Include only patients with known or suspected, acute CNS disease. Do not assess within 2 hours of sedation, paralysis, or anesthesia. If there is constant paralysis and/or sedation, use the time period without sedation, paralysis, or anesthesia closest to the PICU admission for scoring. Stupor/coma is defined as GCS score <8 or stupor/coma using other mental status scales.

7. Acid-Base: Use calculated bicarbonate values from blood gases only if total $CO_2$ is not measured routinely. pH and $PCO_2$ may be measured from arterial, capillary, or venous sites.

8. $PaO_2$: Use arterial measurements only.

9. While Blood Corrections: Whole blood measurements should be increased as follows: glucose-10%; sodium-3 mmol/L; potassium-0.4 mmol/L. (Pediatric Reference Ranges, Soldin S. J., Hicks J. M. eds, AACC Press, Washington, D.C., 1995).

10. Nonoperative CV disease includes acute cardiac and vascular conditions as the primary reasons for admission. Cancer and chromosomal anomalies are acute or chronic. Previous PICU admission and pre-PICU CPR refer to the current hospital admission. CPR requires cardiac massage. Post-operative is the initial 24 hours following an OR surgical procedure. Catheterizations are not post-operative. Acute diabetes includes acute manifestation of diabetes (e.g. DKA) as the primary reason for PICU admission. Admission from routine care area includes all inpatient locations except the operation or recovery rooms.

The PRISM III-APS methodology is set forth as follows:

PRISM III-APS

PRISM III Acute Physiology Score based on the first 24 hours of PICU care. Abbreviations: N=neonate (0–<1 month); I=infant (1–<12 months); C=child (12–<=144 months); A=adolescent (>144 months).

Respiratory Rate (HIGH)

| Age | Range | Score |
|---|---|---|
| N | >100 | 8 |
| I | >100 | 8 |
| C | >80 | 8 |
| A | >60 | 8 |

Blood Pressure - Systolic (LOW)

| Age | Range | Score | Range | Score |
|---|---|---|---|---|
| N | <40 | 19 | 40–50 | 4 |
| I | <45 | 19 | 45–55 | 4 |
| C | <55 | 19 | 55–65 | 4 |
| A | <65 | 19 | 65–75 | 4 |

| Age | Range | Score |
|---|---|---|
| N | 51–55 | 2 |
| I | 56–65 | 2 |
| C | 66–75 | 2 |
| A | 76–85 | 2 |

Blood pressure - Diastolic (HIGH)

| Age | Range | Score |
|---|---|---|
| N | >80 | 4 |
| I | >95 | 4 |
| C | >100 | 4 |
| A | >110 | 4 |

Heart Rate (LOW)

| Age | Range | Score |
|---|---|---|
| N | >75 | 6 |
| I | >75 | 6 |
| C | >55 | 6 |
| A | >55 | 6 |

Heart Rate (HIGH)

| Age | Range | Score | Range | Score |
|---|---|---|---|---|
| N | 195–214 | 3 | 215–225 | 5 |
| I | 195–214 | 3 | 215–225 | 5 |
| C | 165–184 | 3 | 185–205 | 5 |
| A | 135–144 | 3 | 145–155 | 5 |

| Age | Range | Score |
|---|---|---|
| N | 225< | 9 |
| I | 225< | 9 |
| C | 205< | 9 |
| A | 155< | 9 |

Creatinine (HIGH)

| Age | Range | Score | Range | Score |
|---|---|---|---|---|
| N | 0.70–0.85 | 1 | 0.85< | 4 |
| I | 0.75–0.90 | 1 | 0.90< | 4 |
| C | 0.75–0.90 | 1 | 0.90< | 4 |
| A | 1.00–1.30 | 1 | 1.30< | 4 |

BUN (HIGH)

| Age | Range | Score | Range | Score |
|---|---|---|---|---|
| N | 12–15 | 5 | 15< | 10 |
| I | 15–20 | 5 | 20< | 10 |
| C | 15–20 | 5 | 20< | 10 |
| A | 15–20 | 5 | 20< | 10 |

$HCO_3$ or Total $CO_2$ (LOW)

| Age | Range | Score | Range | Score |
|---|---|---|---|---|
| All Ages | 17–20 | 1 | <17–14 | 2 |

| Age | Range | Score | Range | Score |
|---|---|---|---|---|
| All Ages | <14–8 | 5 | <8–5 | 6 |

| Age | Range | Score |
|---|---|---|
| All Ages | <5 | 7 | pH (LOW)

| Age | Range | Score | Range | Score |
|---|---|---|---|---|
| All Ages | 7.2–7.28 | 2 | <7.2–7.1 | 3 |

| Age | Range | Score | Range | Score |
|---|---|---|---|---|
| All Ages | <7.1–7.0 | 7 | <7.0 | 11 | pH (HIGH)

| Age | Range | Score | Range | Score |
|---|---|---|---|---|
| All Ages | 7.48–7.55 | 4 | <7.55–7.6 | 7 |

| Age | Range | Score |
|---|---|---|
| All Ages | <7.6 | 12 |

$PCO_2$ (HIGH)

| Age | Range | Score | Range | Score |
|---|---|---|---|---|
| All Ages | 50–60 | 4 | <60–75 | 7 |

| Age | Range | Score |
|---|---|---|
| All Ages | <75 | 12 |

$PCO_2$ (LOW)

| Age | Range | Score | Range | Score |
|---|---|---|---|---|
| All Ages | 50–60 | 5 | <50–42 | 7 |

| Age | Range | Score |
|---|---|---|
| All Ages | <42 | 11 |

Hemoglobin (HIGH)

| Age | Range | Score |
|---|---|---|
| All Ages | >14 | 3 |

-continued

Platelet (LOW)

| Age | Range | Score | Range | Score |
|---|---|---|---|---|
| All Ages | 1000–200 | 2 | <100–50 | 7 |

| Age | Range | Score | | |
|---|---|---|---|---|
| All Ages | <50 | 11 | | |

WBC (LOW)

| Age | Range | Score | Range | Score |
|---|---|---|---|---|
| All Ages | 4.5–6.0 | 2 | <4.5–3.0 | 4 |

| Age | Range | Score | | |
|---|---|---|---|---|
| All Ages | <3.0 | 11 | | |

PT (HIGH)

| Age | Range | Score | Range | Score |
|---|---|---|---|---|
| All Ages | 16.5–22 | 3 | <22 | 6 |

PTT (HIGH)

| Age | Range | Score | Range | Score |
|---|---|---|---|---|
| All Ages | 16.5–22 | 3 | <22 | 6 |

Calcium (Ca, HIGH)

| Age | Range | Score | Range | Score |
|---|---|---|---|---|
| All Ages | 10.5–12.0 | 6 | <12.0 | 7 |

Glucose (LOW)

| Age | Range | Score | Range | Score |
|---|---|---|---|---|
| All Ages | <60–50 | 1 | <50–40 | 5 |
| All Ages | <40–30 | 6 | g3D | 8 |

Glucose (HIGH)

| Age | Range | Score | Range | Score |
|---|---|---|---|---|
| All Ages | 160–200 | 1 | >200–250 | 1 |
| All Ages | >250–400 | 2 | >400 | 3 |

Sodium (Na, HIGH)

| Age | Range | Score | Range | Score |
|---|---|---|---|---|
| All Ages | 146–150 | 1 | >150 | 3 |

Temperature (rectal, oral, blood, axillary) (LOW)

| Age | Range | Score | | |
|---|---|---|---|---|
| All Ages | <33 | 11 | | |

Temperature (rectal, oral, blood, axillary) (HIGH)

| Age | Range | Score | | |
|---|---|---|---|---|
| All Ages | >40 | 9 | | |

Pupils, size and reactivity (WORST)

| Age | Range | Score | Range | Score |
|---|---|---|---|---|
| All Ages | both fixed | 31 | one fixed | 1 |

Coma (WORST)

| Age | Range | Score | | |
|---|---|---|---|---|
| All Ages | stupor/coma | 13 | | |

Figure 3:
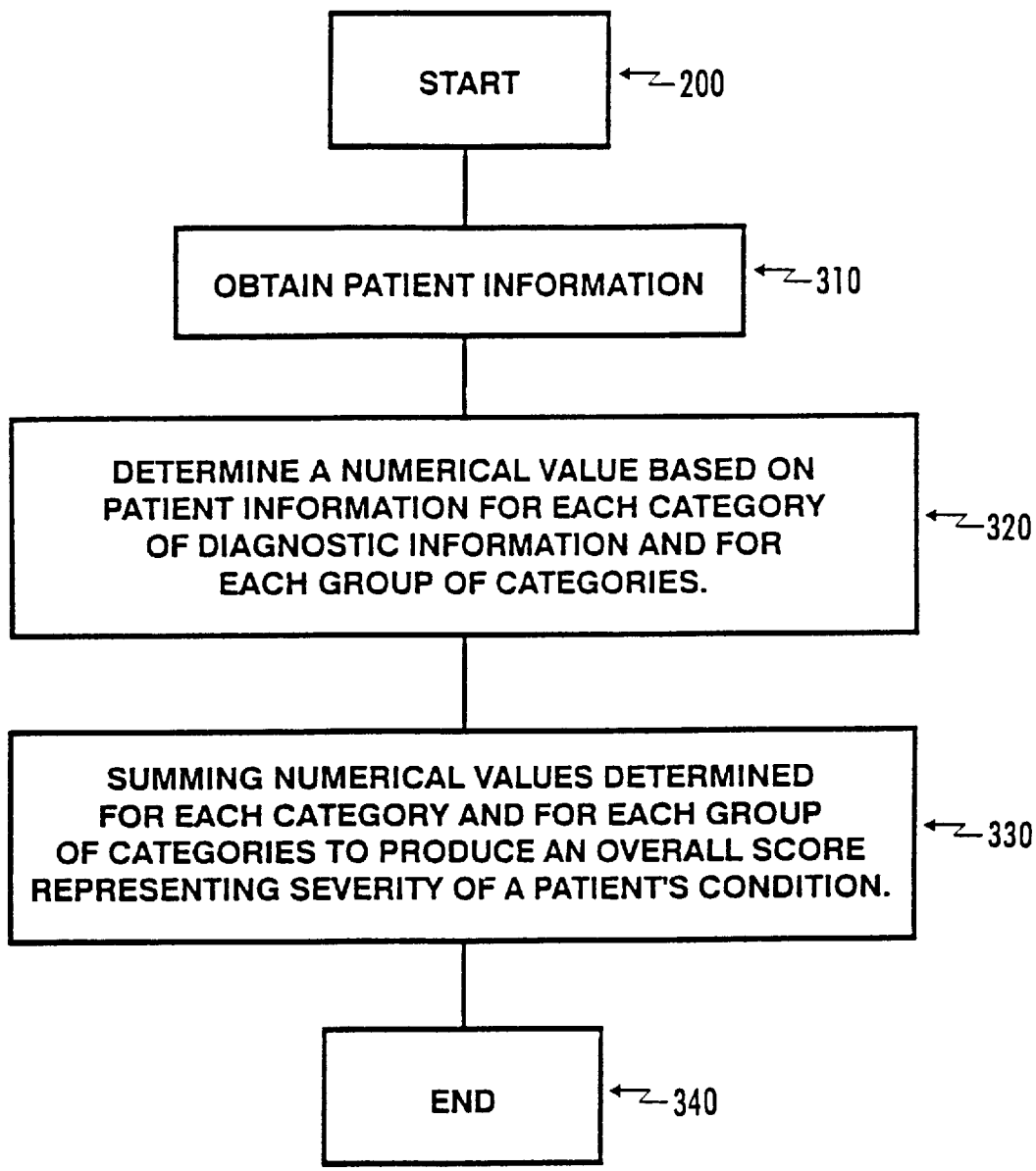
FIG. 3 illustrates a computer implemented process for rating the severity of condition of a patient in a pediatric hospital.

Generally, each of these scoring systems, processes or methodologies illustrated generally in FIG. 3 is implemented as a computer implemented process, starting with item 300 and with obtaining patient information as indicated at Item 310. Again, patient information is preferably obtained in automated form. At Item 320, a numerical value based on patient information is assigned for each category of diagnostic information and for each group of categories. Rules and guidelines for the assignment of numerical values are set forth in the detailed descriptions of the scoring methodologies set forth above corresponding respectively to PRISM, PRISM III(-12 and-24) and PRISM III-APS. Each of the scoring methodologies provides a measure of the severity of the patient's condition.

The PRISM III-12 methodology is preferred for evaluating PICU or pediatric hospital quality. The PRISM III-24 methodology is preferred for assessment of mortality risk of individual patients. PRISM III-APS is used as an index of relative physiologic status.

Figure 4:
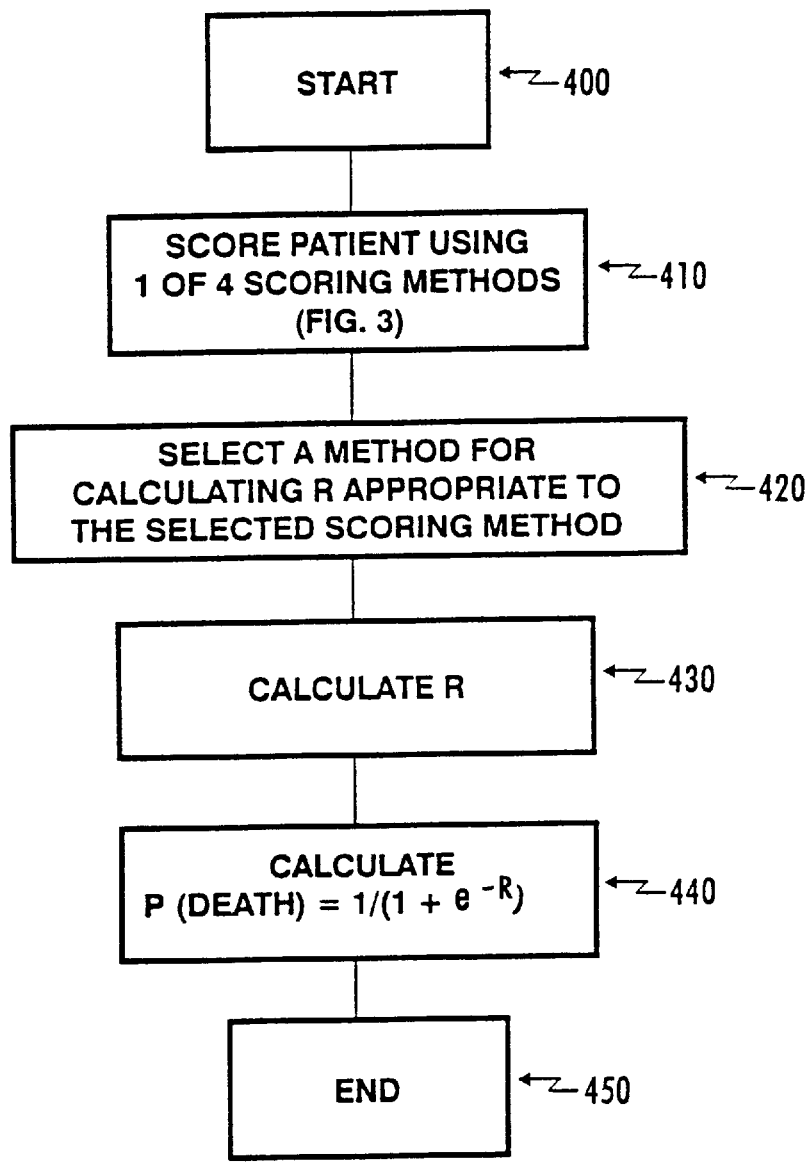
FIG. 4 is a flow chart of a computer implemented process for determining probability of death in a pediatric intensive care unit.

FIG. 4 illustrates a computer implemented method for deriving from the patient's score, achieved under the scoring methodologies, a probability of death. The process begins at step 400. At 410, a patient is scored utilizing one of the four scoring methods discussed in conjunction with FIG. 3. Each of the scoring methodologies has associated with it a plurality of different methods for determining a value R. At step 420, the user selects one of those methods for calculating the value R for the scoring methodology selected at block 410. The alternative equations for R represent progressively more refined calculations. For some purposes, the first equation may be a sufficient approximation. The last formulation of R is the most accurate and is therefore generally preferred. The cost and difficulty of data gathering may dictate which equation for R may be preferred for a particular study.

At block 30, the value of R is determined in accordance with the selected equation and methodology and at Item 440 the variable R is utilized to calculate a probability of death in accordance with the equation given in that block. The process ends at block 450.

Figure 5:
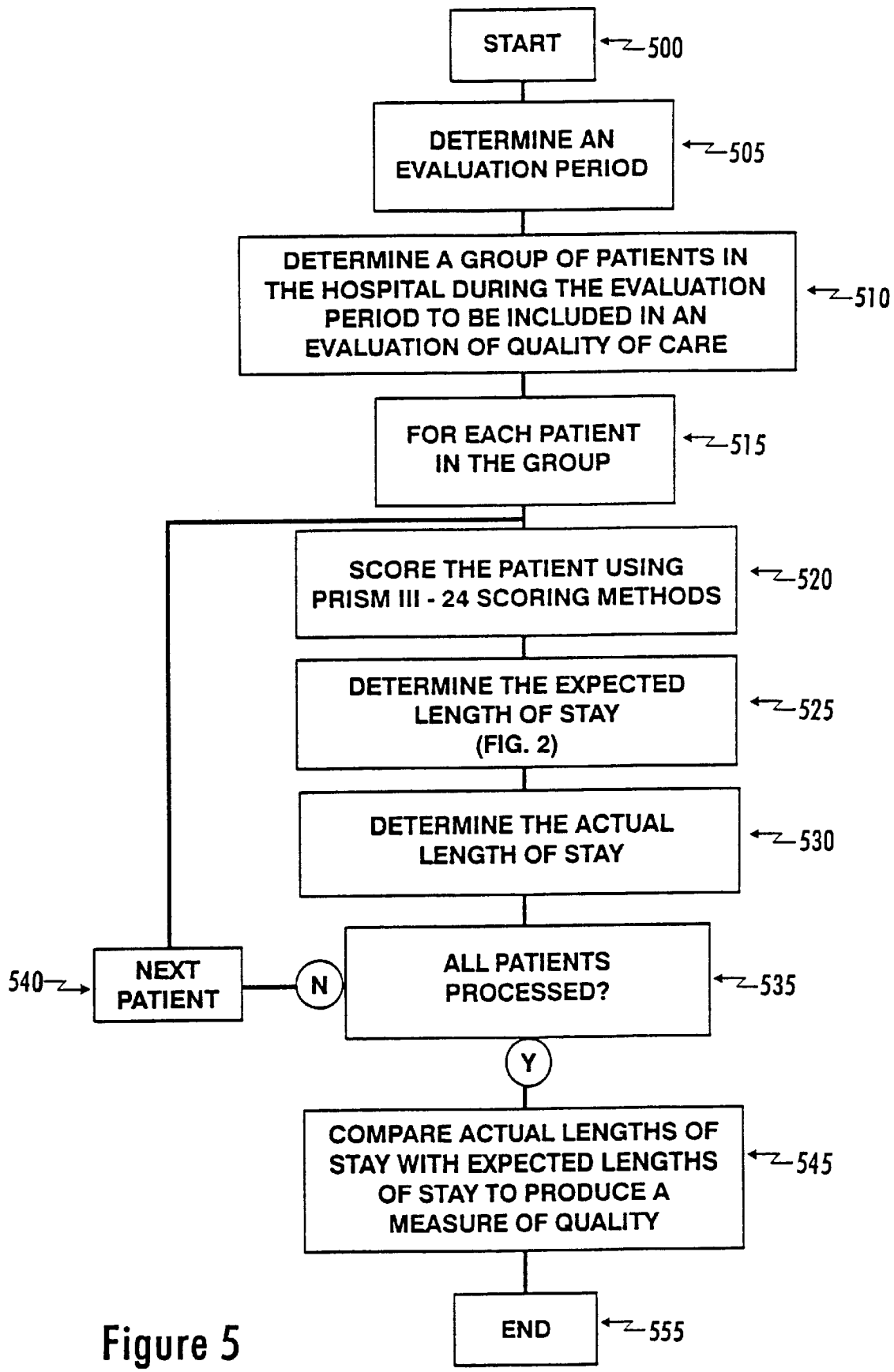
FIG. 5 is a flow chart of one embodiment of a computer implemented process for measuring quality of care in a pediatric hospital based on length of stay.

FIG. 5 is a flow chart of a computer implemented process of one embodiment of the invention which measures the quality of care at a pediatric hospital utilizing expected lengths of stay.

The process begins at step 500 and at step 505, a user determines an evaluation period for the determination of quality. At step 510, the user also determines a group of patients in the hospital during the evaluation period to be included in the evaluation of quality of care. Preferably, this is done by selecting all patients whose date of disposition fails within the evaluation period. Alternatively, a subset of those patients might be selected when only one department or operating section of the hospital is to be evaluated. For each patient in this group of patients (515), the patients are scored, preferably using the PRISM III-24 scoring methodology (520) and the expected length of stay for the patient is calculated as discussed in conjunction with FIG. 2, above. At 530, the actual length of stay for the patient is determined from hospital records for the patients in the group. At Item 535, a check is made to see if all patients have been processed, and, if not, next patient records are obtained and the loop traversed again until all patients are processed. At block 545, the actual lengths of stay for the set of patients in the group are compared with expected lengths of stay to produce a measure of quality and the process ends at 550. For example, if actual lengths of stay in a particular hospital averaged 10 days and the expected lengths of stay of an identical population averaged only 8 days, one might infer that the hospital was not treating its patients efficiently.

Note that an average of length of stays unweighted for severity of illness is not a good indicator of quality because the patient mix in a particular hospital varies from time to time depending upon the severity of conditions of the patient set in the hospital at a particular point in time. By scoring the patients using the methodology set forth in this invention, an expected length of stay is determined which is weighted in accordance with the severity of the condition of the patient. Thus, patient mix is removed as a factor in comparative evaluations of quality.

Figure 6:
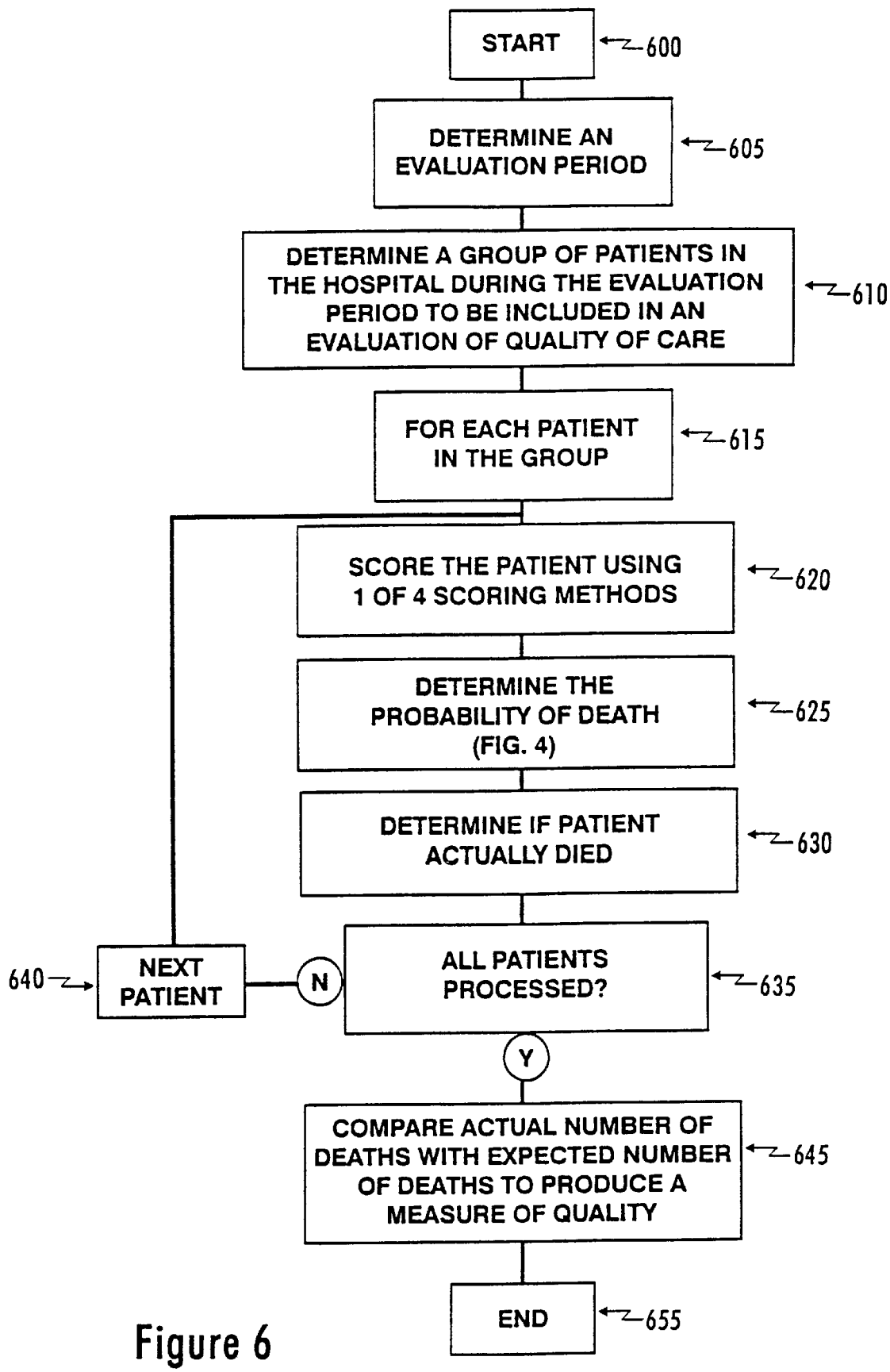
FIG. 6 is a flow chart of another embodiment of a computer implemented process for measuring quality of care in a pediatric hospital based on number of deaths.

FIG. 6 is substantially identical to FIG. 5 except that block 625 is changed to determine the probability of death rather than the expected length of stay; block 630 has been changed to determine if the patient actually died rather than to determine the actual length of stay; and block 645 is changed to compare the actual number of deaths with the expected number of deaths to produce a measure of quality. The probability of death in block 625 is determined in accordance with the methodology set forth and discussed in FIG. 4 above.

Figure 7:
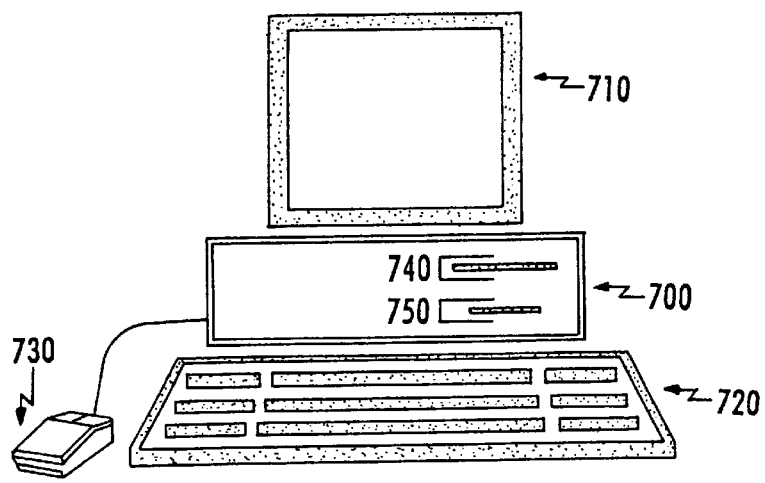
FIG. 7 illustrates one example of a computer on which the computer implemented processes of the invention can be run.

The computer implemented processes described above are preferably run on a computer and conveniently run on a personal computer class of device such as shown in FIG. 7. Such a device consists of a central processing unit 700. They display 710, a keyboard 720, and a mouse 730. Disk drives are indicated at 740 and 750.

Figure 8:
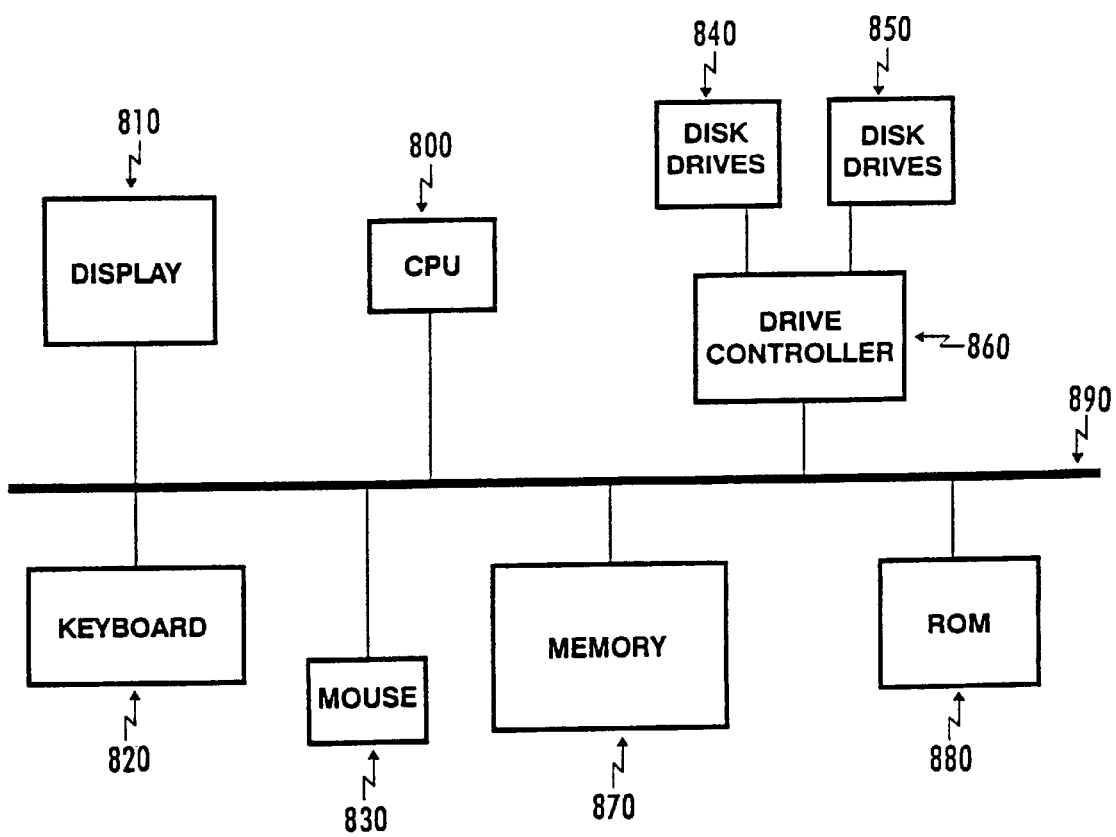
FIG. 8 is a block diagram illustrating at a high level the computer architecture of a computer of the type shown in FIG. 7.

FIG. 8 illustrates a hardware architecture of a typical device of the type shown in FIG. 7. A bus 890 forms an interconnection medium for the various components of the computer. CPU 800 is the main calculating element for the computer. Display 810 displays information and I/O devices 820 and 830, typically a keyboard and a mouse have their corresponding illustrations in FIG. 7. Disk drives 840 and 850 corresponding to those of FIG. 7 are interfaced by a drive controller 860 to the bus 890. Similarly, memory for the CPU 800 is found at block 870 and 880. Typically, certain bootstrap routines and other software are located semipermanently or permanently in ROM 880 to facilitate with the start-up of the computer.

In operation, the computer implemented processes shown above are loaded into memory 89, typically under control of an operating system and typically the loading occurs by disk drives 840 or 850. Drives 840 and 850 are drives which accommodate storage media such as magnetic storage or optical storage.

Figure 9:
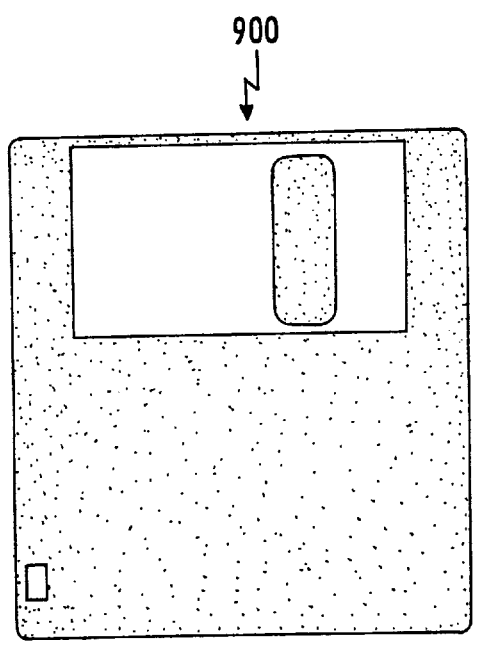

FIG. 9 illustrates a magnetic disk typically utilized for storing computer programs such as the computer implemented processes described herein. Diskettes of this nature are loaded into the disk drives and then loaded into the computer's memory for operation. While it is clear that a magnetic diskette is illustrated in FIG. 9, any storage medium capable of storing the computer implemented inventions of this disclosure can be utilized.

This has thus been described a system and method for achieving the advantages of the invention set forth above.

In this disclosure, there is shown an described only the preferred embodiment of the invention, but, as aforementioned, it is to be understood that the invention is capable of use in various other combinations and environments and is capable of changes or modifications within the scope of the inventive concept as expressed herein.

What is claimed is:

1. A computer implemented method for allocating beds for a pediatric hospital comprising:

a. obtaining patient information for each patient admitted to the hospital, and determining a score, PRISM III-24, for the patient;

b. calculating an estimated duration, LOS, for the hospital stay of said each patient based on said score as follows:

$$LOS = e^{(b_{PRISM\ III\ 24} + d_0 + d_1 x_1 + \ldots + d_p x_p)}$$

where $b_{PRISM\ III\ 24}$=coefficients from PRISM III-24 ranges as follows:

| PRISM III-24 | $b_{PRISM\ III\ 24}$ |
   |---|---|
   | 0–13 | 0.05823 + 0.530 (PRISM III-24) |
   | 14–16 | 1.2725 |
   | 17–23 | 3.3365 − 0.1214 (PRISM III-24) |
   | 24–27 | 0.5442 |
   | 28–34 | 0.3564 |
   | >34 | 0 | where $d_0 = 0.4167$,
   and where $d_i$ are the coefficients for the following diagnostic groups and $x_i=1$ if the condition is present and $x_i=0$ if the condition is not present, the diagnostic groups and their coefficients being:

| Diagnosis | $d_i$ |
   |---|---|
   | Oncologic disease | +0.1529 |
   | Pneumonia (viral or bacterial) | +0.4291 |
   | Central Nervous System infections | +0.3973 |
   | Drug overdose | −0.1973 |
   | ICU admission for treatment of acute diabetes or its complications | −0.2528 |
   | ICU admission for treatment of congenital heart disease (non-operative) | +0.1749 |
   | Postoperative | +0.1529 |
   | Admission from inpatient area (excluding operating or recovery room | +0.2554 |
   | Previous ICU admission during the current hospitalization | +0.1754 |
   | Use of mechanical ventilation during the first 24 hours | +0.5102 | c. determining the number of hospital beds in use at a point in time using the dates of admission and LOS determined for each patient admitted to said hospital, and d. allocating hospital beds to patients awaiting admission based on said number of hospital beds in use.

2. A computer readable storage medium containing a program implementing the method of claim 1.

3. A computer implemented method for determining the probable length of stay of a patient in a pediatric intensive care unit, comprising:

a. recording patient information for said patient and determining a score, PRISM III-24, for the patient;

b. calculating probable length of stay, LOS, for said patient based on said score as follows:

$$LOS = e^{(b_{PRISM\ III\ 24} + d_0 + d_1 x_1 + \ldots + d_p x_p)}$$

where $b_{PRISM\ III\ 24}$=coefficients from PRISM III-24 ranges as follows:

| PRISM III-24 | $b_{PRISM\ III\ 24}$ |
   |---|---|
   | 0–13 | 0.05823 + 0.530 (PRISM III-24) |
   | 14–16 | 1.2725 |
   | 17–23 | 3.3365 − 0.1214 (PRISM III-24) |
   | 24–27 | 0.5442 |
   | 28–34 | 0.3564 |
   | >34 | 0 | where $d_0 = 0.4167$,
   and where $d_i$ are the coefficients for the following diagnostic groups and $x_i=1$ if the condition is present and $x_i=0$ if the condition is not present, the diagnostic groups and their coefficients being:

| Diagnosis | $d_i$ |
|---|---|
| Oncologic disease | +0.1529 |
| Pneumonia (viral or bacterial) | +0.4291 |
| Central Nervous System infections | +0.3973 |
| Drug overdose | −0.1973 |
| ICU admission for treatment of acute diabetes or its complications | −0.2528 |
| ICU admission for treatment of congenital heart disease (non-operative) | +0.1749 |
| Postoperative | +0.1529 |
| Admission from inpatient area (excluding operating or recovery room) | +0.2554 |
| Previous ICU admission during the current hospitalization | +0.1754 |
| Use of mechanical ventiliation during the first 24 hours | +0.5102 | c. allocating intensive care unit resources based on calculated probable length of stay.

4. A computer readable storage medium containing a program implementing the method of claim 3.

5. A computer implemented method of objectively rating the severity of a patient's condition comprising:

a. obtaining patient information for a patient;

b. determining a numerical value for each of the following categories of information for the patient by assigning the value indicated by the range in which the patient's information falls or otherwise assigning 0:

Cardiovascular/Neurologic Vital Signs

1. Systolic blood pressure (mm Hg)

| Age | Value = 3 | Value = 7 |
|---|---|---|
| Neonate | 40–55 | <40 |
| Infant | 45–65 | <45 |
| Child | 55–75 | <55 |
| Adolescent | 65–85 | <65 |

2. Temperature (degrees Centrigrade)
   All ages <33 or >40.0  Value = 3
3. Mental Status
   All ages Stupor/Coma (GCS <8)  Value = 5
4. Heart Rate (beats per minute)

| Age | Value = 3 | Value = 7 |
|---|---|---|
| Neonate | 215–255 | <225 |
| Infant | 215–225 | <225 |
| Child | 185–205 | <205 |
| Adolescent | 145–155 | <155 |

5. Pupillary Reflexes
   All Ages One fixed, one reactive  Value = 7
   All Ages Both fixed  Value = 11

Acid-Base/Blood Gases

1. Acidosis (Total $CO_2$ (mmol/L) or pH)
   All Ages pH 7.0–7.28 or total $CO_2$ 5–16.9  Value = 2
   All Ages pH <7.0 or total $CO_2$ <5  Value = 6
2. pH
   All Ages 7.48–7.55  Value = 2
   All Ages >7.55  Value = 3
3. $PCO_2$ (mm Hg)
   All Ages 50.0–75.0  Value = 1
   All Ages >75.0  Value = 3
4. Total $CO_2$ (mmol/L)
   All Ages .34.0  Value = 4
5. $PaO_2$ (mm Hg)
   All Ages 42.0–49.9  Value = 3
   All Ages >42.0  Value = 6

Chemistry Tests

1. Glucose
   All Ages >200 mg/dL or >11.0 mmol/L  Value = 2
2. Creatinine
   Value = 2

| Neonate | >0.85 mg/dL or >75 μmol/L |
| Infant | >0.90 mg/dL or >80 μmol/L |
| Child | >0.90 mg/dL or >80 μmol/L |
| Adolescent | >1.30 mg/dL or >115 μmol/L |

3. Potassium (mmol/L)
   All Ages > 6.9  Value = 3
4. Blood Urea Nitrogen (BUN)
   Value = 3

| Neonate | >11.9 or >4.3 mmol/L |
| All Other Ages | >14.9 or >5.4 mmol/L |

Hematology Tests

1. White Blood Cell Count (cells/$mm^3$)
   All ages <3,000  Value = 4
2. Platelet Count (cells/$mm^3$)
   All Ages  100,000–200,000  Value = 2
   All Ages  50,000–99,999  Value = 4
   All Ages <50,000  Value = 5
3. Prothrombin Time (PT) or
   Partial Thromboplastin Time (PTT) seconds)
   Value = 3

| Neonate | PT >22.0 or PTT >85.0 |
| All Other Ages | PT >22.0 or PTT >57.0 | c. summing all values to produce an overall score, PRISM III, which is an objective rating of the severity of the patient's condition, and d. allocating resources to a patient based on the overall score.

6. A computer readable storage medium containing a program implementing the method of claim 5.

7. The computer method of objectively rating the severity of a patient's condition as set forth in claim 5, further comprising:

calculating a probability of death of the patient during the patient's admission to a pediatric intensive care unit as follows:

$P(death)=1/(1+e^{-R})$, where R is a function of PRISM III information gathered over the first 12 hours of a patient's admission to the hospital and ln is the natural logarithm.

8. The computer method of claim 7 in which:
R=−5.2560+0.2759(PRISM III-12).

9. The method of claim 7 in which:
R=−5.5434+0.3441(PRISM III-12)−0.00267(PRISM III-12)$^2$, where (PRISM III-12)$^2$ is the PRISM III-12 term squared.

10. The computer method of claim 7 in which:
R=−5.8294+0.3318(PRISM III-12)−0.00265(PRISM III-12)$^2$+0.4899(Pre-ICU care area)−0.6619(operative status)+0.6620(previous ICU admission)−1.7463(acute diagnosis of diabetes)+0.5148(chromosomal anomaly)+0.7634(acute or chronic oncologic disease)+0.6737(acute nonoperative cardiovascular disease)+1.1103(pre-ICU cardiac massage), where pre-ICU care area=1 if the admission is from an inpatient location, excluding the operating room or recovery room; otherwise it=0;

where operative status=1 if postoperative admission; otherwise it=0;

where previous ICU admission=1 if there was a previous ICU admission during current hospitalization; otherwise it=0;

where acute diagnosis of diabetes=1 if acute problem requiring ICU admission is associated with diabetes (such as ketoacidosis); otherwise it=0;

where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where Acute nonoperative cardiovascular disease=1 if the acute problem requiring ICU admission is associated with congenital or acquired cardiac or vascular disease, excluding postoperative care; otherwise it=0; and where Pre-ICU cardiac massage=1 if there has been closed or open chest cardiac massage (cardiac compressions) immediately prior to the PICU admission; otherwise it=0.

11. A computer implemented method for evaluating the quality of care of a pediatric hospital, comprising:

for a group of patients in the hospital during a period of interest, determining a probability of death for each patient in said group in accordance with claim 4, and further comprising the steps of:

e. using the set of probabilities of death for each patient in said group, determining an expected number of deaths for said group;

f. for said group of patients, determining the actual number of deaths, and g. determining a measure of quality using the expected number of deaths and the actual number of deaths.

12. The computer method of objectively rating the severity of a patient's condition as set forth in claim 7, further comprising:

calculating a probability of death of the patient during the patient's admission to a pediatric intensive care unit as follows:

$P(\text{death}) = 1/(1+e^{-R})$, where R is a function of PRISM III information gathered over the first 24 hours of a patient's admission to the hospital.

13. The computer method of claim 12 in which:

$R = -5.5743 + 0.2652(\text{PRISM III-24})$.

14. The computer method of claim 12 in which:

$R = -6.0396 + 0.3544(\text{PRISM III-24}) - 0.00304(\text{PRISM III-24})^2$, where $(\text{PRISM III-12})^2$ is the PRISM III-12 term squared.

15. The computer method of claim 12 in which:

$R = -6.2833 + 0.3377(\text{PRISM III-24}) - 0.00283(\text{PRISM III-24})^2 + 0.4536(\text{Pre-ICU care area}) - 0.6966(\text{operative status}) + 0.6650(\text{previous ICU admission}) - 1.6763(\text{acute diagnosis of diabetes}) + 0.5568(\text{chromosomal anomaly}) + 0.7746(\text{acute or chronic oncologic disease}) + 0.6467(\text{acute nonoperative cardiovascular disease}) + 1.1197(\text{pre-ICU cardiac massage})$ where pre-ICU care area=1 if the admission is from an inpatient location, excluding the operating room or recovery room; otherwise it=0;

where operative status=1 if postoperative admission; otherwise it=0;

where previous ICU admission=1 if there was a previous ICU admission during current hospitalization; otherwise it=0;

where acute diagnosis of diabetes=1 if acute problem requiring ICU admission is associated with diabetes (such as ketoacidosis); otherwise it=0;

where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where Acute nonoperative cardiovascular disease=1 if the acute problem requiring ICU admission is associated with congenital or acquired cardiac or vascular disease, excluding postoperative care; motherwise it=0; and where Pre-ICU cardiac massage=1 if there has been closed or open chest cardiac massage (cardiac compressions) immediately prior to the PICU admission; otherwise it=0.

16. A computer readable storage medium containing a program implementing the method of claim 12.

17. A computer implemented method of objectively rating the severity of a patient's condition comprising:

a. obtaining patient information for a patient based on the first 24 hours after admission;

b. determining a numerical value for each of the following categories of information for the patient by assigning the value indicated by the range in which the patient's information falls or otherwise assigning 0:

| Age | Range | Score | Range | Score |
|---|---|---|---|---|
| Respiratory Rate (HIGH) | | | | |
| N | >100 | 8 | | |
| I | >100 | 8 | | |
| C | >80 | 8 | | |
| A | >60 | 8 | | |
| Blood Pressure - Systolic (LOW) | | | | |
| N | <40 | 19 | 40–50 | 4 |
| I | <45 | 19 | 45–55 | 4 |
| C | <55 | 19 | 55–65 | 4 |
| A | <65 | 19 | 65–75 | 4 |
| N | 51–55 | 2 | | |
| I | 56–65 | 2 | | |
| C | 66–75 | 2 | | |
| A | 76–85 | 2 | | |
| Blood Pressure - Diastolic (HIGH) | | | | |
| N | >80 | 4 | | |
| I | >95 | 4 | | |
| C | >100 | 4 | | |
| A | >110 | 4 | | |
| Heart Rate (LOW) | | | | |
| N | >75 | 6 | | |
| I | >75 | 6 | | |
| C | >55 | 6 | | |
| A | >55 | 6 | | |
| Heart Rate (HIGH) | | | | |
| N | 195–214 | 3 | 215–225 | 5 |
| I | 195–214 | 3 | 215–225 | 5 |
| C | 165–184 | 3 | 185–205 | 5 |
| A | 135–144 | 3 | 145–155 | 5 |
| N | 225< | 9 | | |
| I | 225< | 9 | | |
| C | 205< | 9 | | |
| A | 155< | 9 | | |
| Creatinine (HIGH) | | | | |
| N | 0.70–0.85 | 1 | 0.85< | 4 |
| I | 0.75–0.90 | 1 | 0.90< | 4 |
| C | 0.75–0.90 | 1 | 0.90< | 4 |
| A | 1.00–1.30 | 1 | 1.30< | 4 |

-continued

| Age | Range | Score | Range | Score |
|---|---|---|---|---|
| BUN (HIGH) | | | | |
| N | 12–15 | 5 | 15< | 10 |
| I | 15–20 | 5 | 20< | 10 |
| C | 15–20 | 5 | 20< | 10 |
| A | 15–20 | 5 | 20< | 10 |
| HCO$_3$ or Total CO$_2$ (LOW) | | | | |
| All Ages | 17–20 | 1 | <17–14 | 2 |
| All Ages | <14–8 | 5 | <8–5 | 6 |
| All Ages | <5 | 7 | | |
| pH (LOW) | | | | |
| All Ages | 7.2–7.28 | 2 | <7.2–7.1 | 3 |
| All Ages | <7.1–7.0 | 7 | <7.0 | 11 |
| pH (HIGH) | | | | |
| All Ages | 7.48–7.55 | 4 | <7.55–7.6 | 7 |
| All Ages | <7.6 | 12 | | |
| PCO$_2$ (HIGH) | | | | |
| All Ages | 50–60 | 4 | <60–75 | 7 |
| All Ages | <75 | 12 | | |
| PCO$_2$ (LOW) | | | | |
| All Ages | 50–60 | 5 | <50–42 | 7 |
| All Ages | <42 | 11 | | |
| Hemoglobin (HIGH) | | | | |
| All Ages | >14 | 3 | | |
| Platelet (LOW) | | | | |
| All Ages | 1000–200 | 2 | <100–50 | 7 |
| All Ages | <50 | 11 | | |
| WBC (LOW) | | | | |
| All Ages | 4.5–6.0 | 2 | <4.5–3.0 | 4 |
| All Ages | <3.0 | 11 | | |
| PT (HIGH) | | | | |
| All Ages | 16.5–22 | 3 | <22 | 6 |
| PTT (HIGH) | | | | |
| All Ages | 16.5–22 | 3 | <22 | 6 |
| Calcium (Ca, HIGH) | | | | |
| All Ages | 10.5–12.0 | 6 | <12.0 | 7 |
| Glucose (LOW) | | | | |
| All Ages | <60–50 | 1 | <50–40 | 5 |
| All Ages | <40–30 | 6 | <30 | 8 |
| Glucose (HIGH) | | | | |
| All Ages | 160–200 | 1 | >200–250 | 1 |
| All Ages | >250–400 | 2 | >400 | 3 |
| Sodium (Na, HIGH) | | | | |
| All Ages | 146–150 | 1 | >150 | 3 |
| Temperature (rectal, oral, blood, axillary) (LOW) | | | | |
| All Ages | <33 | 11 | | |
| Temperature (rectal, oral, blood, axillary) (HIGH) | | | | |
| All Ages | >40 | 9 | | |
| Pupils, size and reactivity (WORST) | | | | |
| All Ages | both fixed | 31 | one fixed | 1 |
| Coma (WORST) | | | | |
| All Ages | stupor/coma | 13 | | | where N=neonate (0–<1 month); I=infant (1–<12 months); C=child (12–<=144 months); A=adolescent (>144 months);

c. summing all values to produce an overall score, PRISM III-APS, which is an objective rating of severity of the patient's condition; and d. allocating resources to a patient based on the severity of the patient's condition.

18. A computer readable storage medium containing a program implementing the method of claim 17.

19. The computer method of objectively rating the severity of a patient's condition as set forth in claim 17, further comprising:

calculating a probability of death of the patient during the patient's admission to a pediatric intensive care unit as follows:

P(death)=1/(1+e$^{-R}$), where R is a function of PRISM III-APS information gathered over the first 24 hours of a patient's admission to the hospital and ln is the natural logarithm.

20. The computer method of claim 19 in which:
R=−5.4935+0.1016(PRISM III-APS).

21. The computer method of claim 19 in which:
R=−6.0176+0.1410(PRISM III-APS)−0.00051(PRISM III-APS)$^2$, where (PRISM III-APS)$^2$ is the PRISM III-APS term squared.

22. The computer method of claim 19 in which:
R=−7.0928+0.0706(PRISM III-APS)+0.8080[ln(PRISM III-APS+1)], where ln is the natural logarithm.

23. The computer method of claim 19 in which:
R=7.3309+0.0700(PRISM III-APS)+0.7301[ln(PRISM III-APS+1)]+0.5216(previous ICU care area)−0.5399 (operative status)+0.5921(previous ICU admission)−1.9775(acute diagnosis of diabetes)+0.5572 (chromosomal anomaly)+0.8360(acute or chronic oncologic disease)+0.8266(acute nonoperative cardiovascular disease)+1.0715(pre-ICU cardiac massage), where pre-ICU care area=1 if the admission is from an inpatient location, excluding the operating room or recovery room; otherwise it=0;

where operative status=1 if postoperative admission; otherwise it=0;

where previous ICU admission=1 if there was a previous ICU admission during current hospitalization; otherwise it=0;

where acute diagnosis of diabetes=1 if acute problem requiring ICU admission is associated with diabetes (such as ketoacidosis); otherwise it=0;

where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where Acute nonoperative cardiovascular disease=1 if the acute problem requiring ICU admission is associated with congenital or acquired cardiac or vascular disease, excluding postoperative care; otherwise it=0; and where Pre-ICU cardiac massage=1 if there has been closed or open chest cardiac massage (cardiac compressions) immediately prior to the PICU admission; otherwise it=0.

24. A computer implemented method of objectively rating the severity of a patient's condition comprising:

a. obtaining patient information for a patient;

b. determining a numerical value for each of the following categories of information for the patient by assigning the value indicated by the range in which the patient's information falls or otherwise assigning 0:

| Variable | Age Restrictions and Ranges | | Score |
|---|---|---|---|
| Systolic BP (mm Hg) | Infants | Children | |
| | 130–160 | 150–200 | 2 |
| | 55–65 | 65–75 | |
| | >160 | >200 | 6 |
| | 40–54 | 50–64 | |
| | <40 | <50 | 7 |
| Diastolic BP (mm Hg) | all ages | | 6 |
| | >110 | | |
| HR (beat/min) | Infants | Children | |
| | >160 | >150 | 4 |
| Respiratory rate | Infants | Children | |
| (breath/min) | 61–90 | 51–70 | 1 |
| | >90 | >70 | 5 |
| | Apnea | Apnea | |
| $PaO_2/FIO_2$ [a] | all ages | | |
| | 200–300 | | 2 |
| | <200 | | 3 |
| [Paco₂] $PaCo_2$ [b] (torr) | all ages | | |
| | 51–65 | | 1 |
| | >65 | | 5 |
| Glasgow Coma Score[c] | all ages | | |
| | >8 | | 6 |
| Pupillary Reactions | all ages | | |
| | unequal or dilated | | 4 |
| | fixed and dilated | | 10 |
| PT/PTT | all ages | | |
| | 1.5 × control | | 2 |
| Total bilirubin (mg/dl) | >1 mo | | |
| | >3.5 | | 6 |
| Potassium (mEq/L) | all ages | | |
| | 3.0–3.5 | | 1 |
| | 6.5–7.5 | | |
| | <3.0 | | 5 |
| | >7.5 | | |
| Calcium (mg/dl) | all ages | | |
| | 7.0–8.0 | | 2 |
| | 12.0–15.0 | | |
| | <7.0 | | 6 |
| | >15.0 | | |
| Glucose (mg/dl) | all ages | | |
| | 40–60 | | 4 |
| | 250–400 | | |
| | <40 | | 8 |
| | >400 | | |
| Bicarbonate[d] (MEq/L) | all ages | | |
| | <16 | | 3 |
| | >32 | | | c. summing all values to produce an overall score, PRISM, d. determining the severity of the patient's condition, by calculating a probability of death of the patient during the patient's admission to a pediatric intensive care unit as follows:
P(death)=$1/(1+e^{-R})$, where R is a function of PRISM information gathered over the first 24 hours of a patient's admission to the hospital and ln is the natural logarithm and
R=−6.6129+0.2864(PRISM)−0.00162(PRISM)²−0.7482(operative status)+1.1659(chromosomal anomaly)+1.0794(acute or chronic oncologic disease)+0.6620(pre-ICU care area)+1.3707(pre-ICU cardiac massage), where (PRISM)² is the PRISM term squared, where operative status=1 if postoperative admission; otherwise it=0 where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where pre-ICU care area=1 if the admission is from an inpatient location, excluding the operating room or recovery room; otherwise it=0; and where pre-ICU cardiac massage=1 if there has been closed or open chest cardiac massage (cardiac compressions) immediately prior to the PICU admission; otherwise it=0, and e. allocating resources to a patient based on the severity of the patient's condition.

25. A computer readable storage medium containing a program implementing the method of claim 24.

26. A computer implemented method of objectively rating the severity of a patient's condition comprising:

a. obtaining patient information for a patient;

b. determining a numerical value for each of the following categories of information for the patient by assigning the value indicated by the range in which the patient's information falls or otherwise assigning 0:

| Variable | Age Restrictions and Ranges | | Score |
|---|---|---|---|
| Systolic BP (mm Hg) | Infants | Children | |
| | 130–160 | 150–200 | 2 |
| | 55–65 | 65–75 | |
| | >160 | >200 | 6 |
| | 40–54 | 50–64 | |
| | <40 | <50 | 7 |
| Diastolic BP (mm Hg) | all ages | | 6 |
| | >110 | | |
| HR (beat/min) | Infants | Children | |
| | >160 | >150 | 4 |
| Respiratory rate | Infants | Children | |
| (breath/min) | 61–90 | 51–70 | 1 |
| | >90 | >70 | 5 |
| | Apnea | Apnea | |
| $PaO_2/FIO_2$ | all ages | | |
| | 200–300 | | 2 |
| | <200 | | 3 |
| [Paco₂] $PaCo_2$ (torr) | all ages | | |
| | 51–65 | | 1 |
| | >65 | | 5 |
| Glasgow Coma Score[c] | all ages | | |
| | >8 | | 6 |
| Pupillary Reactions | all ages | | |
| | unequal or dilated | | 4 |
| | fixed and dilated | | 10 |
| PT/PTT | all ages | | |
| | 1.5 × control | | 2 |

-continued

| Variable | Age Restrictions and Ranges | Score |
|---|---|---|
| Total bilirubin (mg/dl) | >1 mo | 5 |
| Potassium (mEq/L) | >3.5 all ages | 6 |
| | 3.0–3.5 | 1 |
| | 6.5–7.5 | |
| | <3.0 | 5 |
| | >7.5 | |
| Calcium (mg/dl) | all ages | |
| | 7.0–8.0 | 2 |
| | 12.0–15.0 | |
| | <7.0 | 6 |
| | >15.0 | |
| Glucose (mg/dl) | all ages | |
| | 40–60 | 4 |
| | 250–400 | |
| | <40 | 8 |
| | >400 | |
| Bicarbonate[d] (MEq/L) | all ages | |
| | <16 | 3 |
| | >32 | | c. summing all values to produce an overall score, PRISM, d. determining the severity of the patient's condition, by calculating a probability of death of the patient during the patient's admission to a pediatric intensive care unit as follows:

$P(\text{death}) = 1/(1+e^{-R})$, where R is a function of PRISM information gathered over the first 24 hours of a patient's admission to the hospital and ln is the natural logarithm and $R = -7.0086 + 0.2312(\text{PRISM}) - 0.00102(\text{PRISM})^2 - 0.9098(\text{operative status}) + 0.6751(\text{chromosomal anomaly}) + 0.9064(\text{acute or chronic oncologic disease}) + 0.9580(\text{pre-ICU care area}) - 1.3455(\text{pre-ICU cardiac massage})$ where $(\text{PRISM})^2$ is the PRISM term squared, where operative status=1 if postoperative admission; otherwise it=0 where chromosomal anomaly=1 if there is a chromosomal anomaly such as extra chromosome, a long or short arm deletion, or a long or short arm addition; otherwise it=0;

where acute or chronic oncologic disease=1 if there is currently or has been a malignant oncologic disease (cancer); otherwise it=0;

where pre-ICU care area=1 if the admission is from an inpatient location, excluding the operating room or recovery room; otherwise it=0; and where pre-ICU cardiac massage=1 if there has been closed or open chest cardiac massage (cardiac compressions) immediately prior to the PICU admission; otherwise it=0, and e. allocating resources to a patient based on the severity of the patient's condition.

27. A computer readable storage medium containing a program implementing the method of claim 26.

* * * * *